(12) United States Patent
Kulkarni et al.

(10) Patent No.: US 11,454,628 B2
(45) Date of Patent: Sep. 27, 2022

(54) ON-SURFACE MASS TAGGING

(71) Applicant: Northeastern University, Boston, MA (US)

(72) Inventors: Pushkar Kulkarni, Boston, MA (US); Poguang Wang, Westborough, MA (US); Roger W. Giese, Hanover, MA (US)

(73) Assignee: Northeastern University, Boston, MA (US)

( * ) Notice: Subject to any disclaimer, the term of this patent is extended or adjusted under 35 U.S.C. 154(b) by 554 days.

(21) Appl. No.: 16/433,617

(22) Filed: Jun. 6, 2019

(65) Prior Publication Data

US 2020/0041500 A1 Feb. 6, 2020

Related U.S. Application Data

(60) Provisional application No. 62/714,954, filed on Aug. 6, 2018.

(51) Int. Cl.
*G01N 33/543* (2006.01)
*G01N 1/40* (2006.01)
(Continued)

(52) U.S. Cl.
CPC ....... *G01N 33/54306* (2013.01); *G01N 1/286* (2013.01); *G01N 1/405* (2013.01);
(Continued)

(58) Field of Classification Search
CPC ............. G01N 33/54306; G01N 1/405; G01N 1/4055; G01N 1/44; G01N 33/54366;
(Continued)

(56) References Cited

U.S. PATENT DOCUMENTS 8,323,983 B2  12/2012  Nazabal et al.
9,404,918 B2   8/2016  D'Aloia et al.
(Continued)

OTHER PUBLICATIONS

Wang, Poguang et al., "Cationic Xylene Tag for Increasing Sensitivity in Mass Spectrometry," American Society for Mass Spectrometry, vol. 26, pp. 1713-1721, Publ. Jun. 27, 2015, DOI: 10.1007/s13361-015-1200-4 (Year: 2015).*
(Continued)

*Primary Examiner* — Jennifer Wecker
*Assistant Examiner* — Michael Paul Shimek
(74) *Attorney, Agent, or Firm* — Dana M. Gordon; Foley Hoag LLP

(57) ABSTRACT

The present disclosure relates to a method for detecting a compound, comprising the steps of: contacting a compound with a solid analytical surface (SAS), thereby forming an SAS with an absorbed compound; contacting the SAS with the absorbed compound with a mass tag, wherein the mass tag reacts with the absorbed compound, thereby forming an SAS with a covalently mass-tagged absorbed compound; and detecting the covalently mass-tagged absorbed compound by mass spectrometry. Also disclosed is a device for collecting breath aerosol, comprising a card or an envelope, wherein the card or the envelope comprise a tab, wherein the tab is a SAS.

12 Claims, 21 Drawing Sheets

(51) Int. Cl.
*G01N 1/44* (2006.01)
*G01N 33/02* (2006.01)
*G01N 33/15* (2006.01)
*G01N 1/28* (2006.01)
*G01N 1/22* (2006.01)

(52) U.S. Cl.
CPC ............. *G01N 1/4055* (2013.01); *G01N 1/44* (2013.01); *G01N 33/02* (2013.01); *G01N 33/15* (2013.01); *G01N 33/54366* (2013.01); *G01N 2001/2223* (2013.01); *G01N 2001/2873* (2013.01); *G01N 2001/4061* (2013.01); *G01N 2458/15* (2013.01); *G01N 2560/00* (2013.01); *G01N 2800/12* (2013.01); *G01N 2800/7028* (2013.01)

(58) Field of Classification Search
CPC ........ G01N 33/02; G01N 33/15; G01N 1/286; G01N 2458/15; G01N 2800/7028; G01N 2800/12; G01N 2560/00; G01N 2001/2873; G01N 2001/4061; G01N 2001/2223; G01N 33/948; G01N 33/92; G01N 2030/009
See application file for complete search history.

(56) References Cited

U.S. PATENT DOCUMENTS

| | | | |
|---|---|---|---|
| 2005/0164402 A1* | 7/2005 | Belisle | B01L 3/502792 436/174 |
| 2010/0003695 A1* | 1/2010 | Geddes | G01N 33/553 435/7.1 |
| 2012/0302907 A1* | 11/2012 | Palmskog | G01N 33/497 600/532 |
| 2014/0121129 A1* | 5/2014 | Chang | C07F 5/022 548/405 |
| 2017/0227545 A1* | 8/2017 | Mitchell | G01N 33/6848 |
| 2021/0340603 A1* | 11/2021 | Giese | C12Q 1/6827 |

OTHER PUBLICATIONS

Mungalachetty, et al., "Mass Spectrometric Analysis of Aldehydes as Biomarkers of Cancer," RISE: 2019 research poster, Northeastern University, Abstract ID#: 2487, <https://repository.library.northeastern.edu/downloads/neu:m0449z27b7datastream_id=content>, 2019. (Year: 2019).*

Dueno et al., "Cesium Promoted O-Alkylation of Alcohols for the Efficient Ether Synthesis," Tetrahedron Letters, 40:1843-1846 (1999).

Giese, "Detection of DNA Adducts by Electron Capture Mass Spectrometry," Chem. Res. In Toxicology, 10(3): 255-270 (1997).

Giese, "Electron-capture mass spectrometry: recent advances," J. Chromatogr. A, 892: 329-346 (2000).

Wang et al., "Cationic Xylene Tag for Increasing Sensitivity in Mass Spectrometry," J. Am. Soc. Mass Spectrom 26(10): 1713-1721 (2015).

Bielicka-Daszkiewicz et al., "Comparison of three derivatization ways in the separation of phenol and hydroquinone from water samples," Journal of Chromatography A, 1052: 233-236 (2004).

Molins Legua et al., "Derivatization on Solid Supports: An Alternative Method for Solution Derivatization of Amines in Several Matrices," Chromatographia, 58: 15-27 (2003).

* cited by examiner

FIG. 4
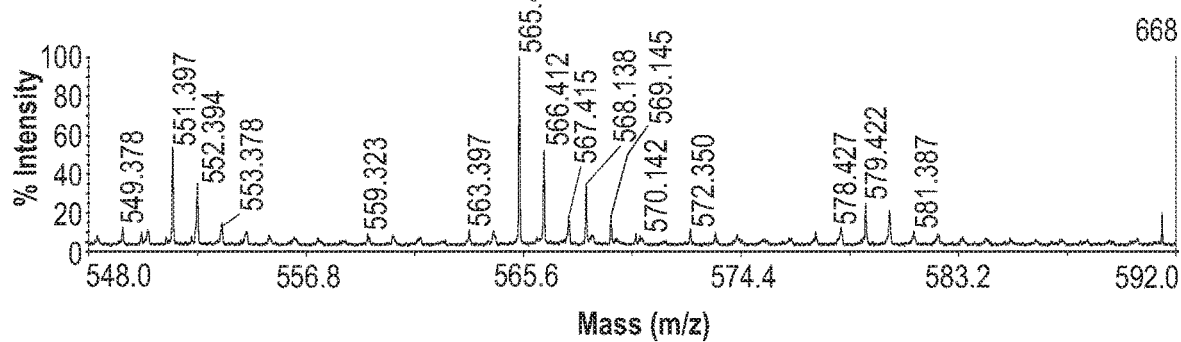
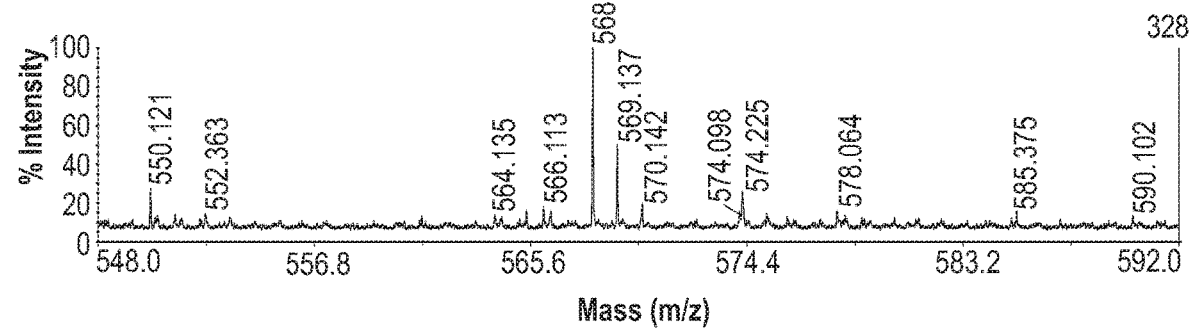
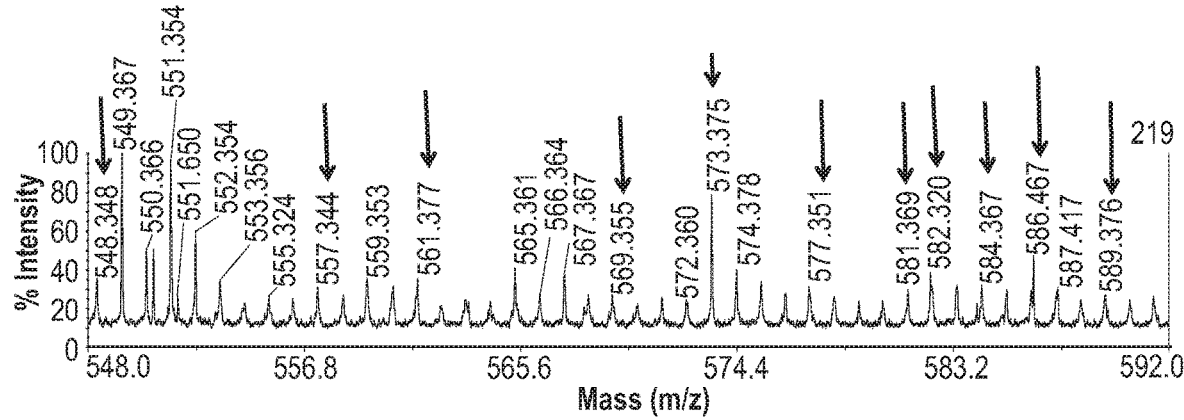

Syringe Device with Compacted SAS

Surface Tagging of Analytes with a CAX Reagent

ON-SURFACE MASS TAGGING

CROSS-REFERENCE TO RELATED APPLICATIONS

This application claims the benefit of priority to U.S. Provisional Application No. 62/714,954, filed Aug. 6, 2018.

GOVERNMENT SUPPORT

This invention was made with Government support under Grant No. ES017198, awarded by National Institutes of Health. The Government has certain rights in the invention.

SUMMARY

Disclosed is a method for detecting a compound, comprising the steps of: contacting a compound with a solid analytical surface (SAS), thereby forming an SAS with an absorbed compound; contacting the SAS with the absorbed compound with a mass tag, wherein the mass tag reacts with the absorbed compound, thereby forming an SAS with a covalently mass-tagged absorbed compound; and detecting the covalently mass-tagged absorbed compound by mass spectrometry. Also disclosed is a device for collecting breath aerosol, comprising a card or an envelope, wherein the card or the envelope comprise a tab, wherein the tab is a SAS.

BACKGROUND

A solid analytical surface (SAS) is a solid surface on which collected compounds begin a detection process such as mass tag mass spectrometry. It is important to detect sorbed (absorbed or adsorbed) compounds collected on a SAS. Examples of the importance of an SAS detection process are as follows. Detection of sorbed compounds from foods, regardless of the mode of collection of the compounds have on a SAS (such as from air that carries a food odor, from a liquid that is a food or has contacted food, or by direct or indirect contact with a surface of interest [primary surface] of a solid or semi-solid food), can help evaluate the freshness, quality, expiration or spoilage of a food. Similarly, detection of SAS-sorbed compounds from alcoholic beverages including wine and beer can help guide production, ingredients, blending, and storage. Similarly, detection of SAS-sorbed compounds from cosmetics, including perfumes, can help evaluate ingredients, quality, reproducibility, safety and appeal to consumers. Similarly, SAS-detection of sorbed compounds from containers for foods can help evaluate leaching of contaminants. Similarly, detection of SAS-sorbed compounds from household air can help reveal indoor toxic exposures. Similarly, detection of SAS-sorbed compounds from human or other biological samples, such as saliva, tears, breath, skin, blood, urine, or feces can help assess health and disease, such as monitoring of drugs including those of multi-substance abuse, and therapy for drug abusers. Similarly, detection of airborne compounds on a primary surface, via swabbing this surface with a SAS, can help reveal illicit transport of drugs or people, or reveal the identity of chemicals or other threat agents released by a terrorist or enemy. SAS testing can also be useful in forensics.

BRIEF DESCRIPTION OF THE DRAWINGS

FIG. 4 shows three mass spectra related to detection of electrophilic compounds in breath according to General Procedure Using CAX-H.

DETAILED DESCRIPTION

Figure 1:
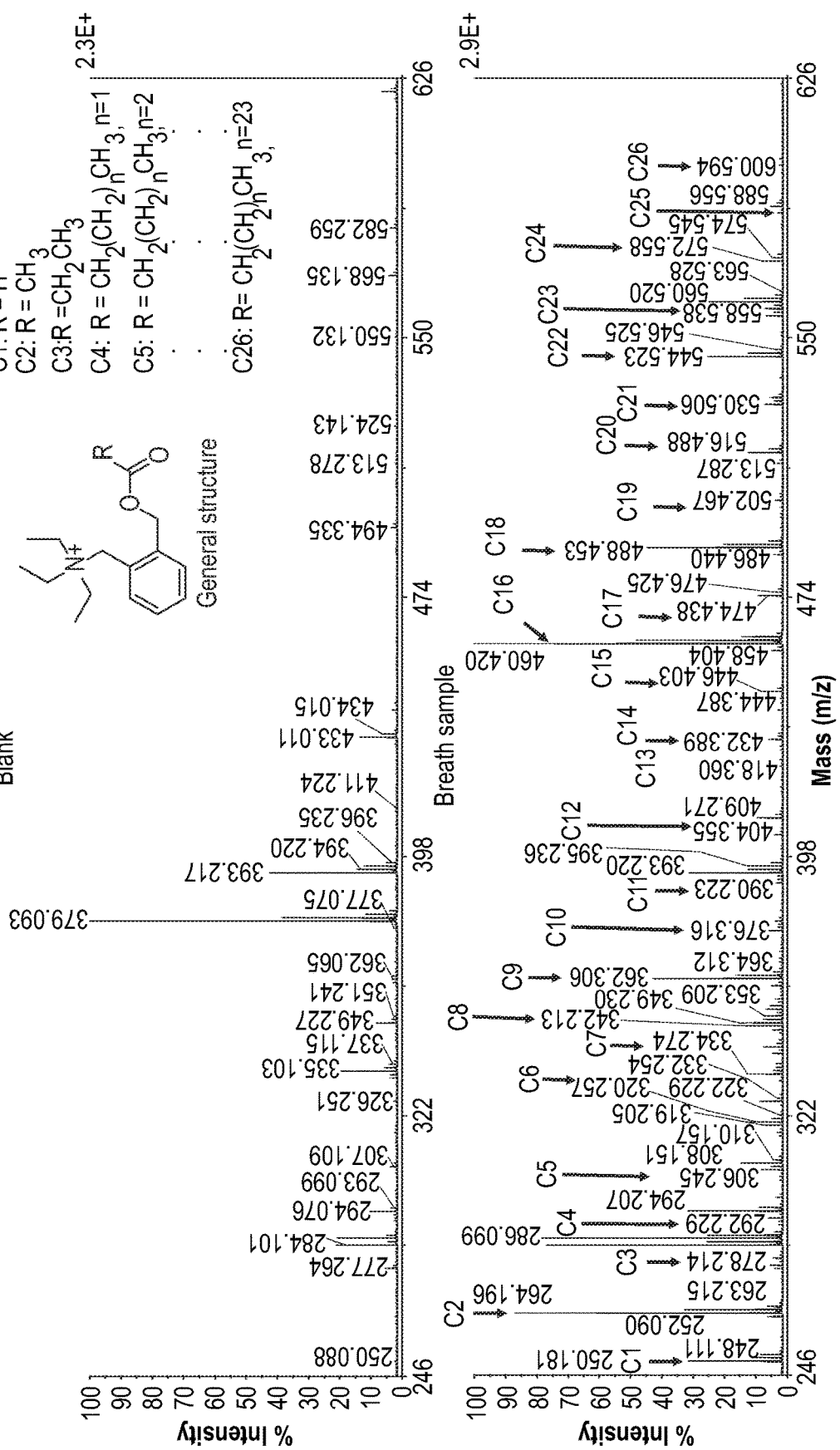
FIG. 1 shows two mass spectra related to detection of $C_1$-$C_{26}$ fatty acids in breath according to General Procedure Using CAX-B. The blank is a control filter paper SAS (i.e., filter paper not exposed to breath).
Figure 2:
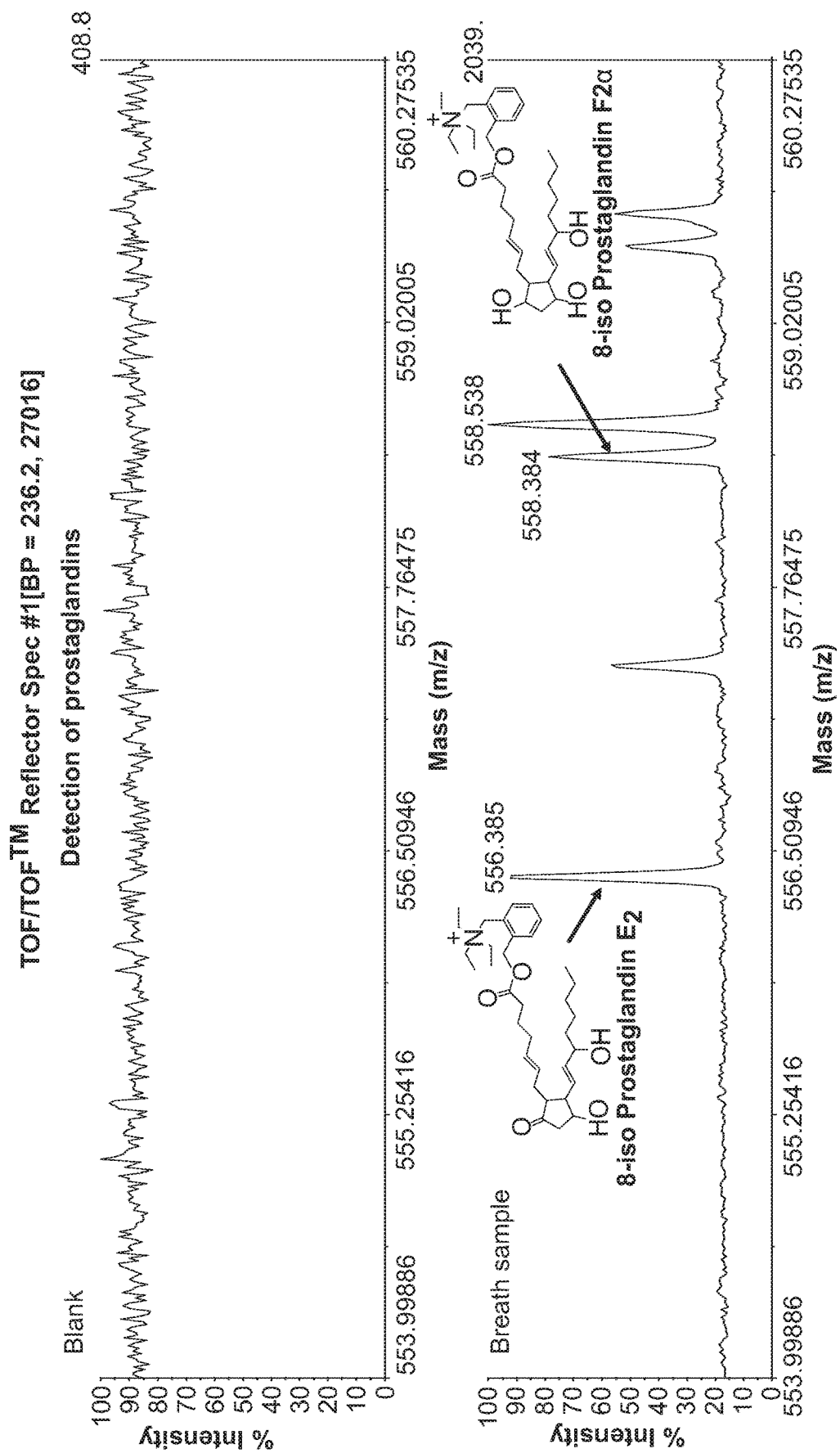
FIG. 2 shows two mass spectra related to detection of prostaglandins in breath according to General Procedure Using CAX-B. The upper mass spectrum is from a blank SAS, as above.
Figure 3:
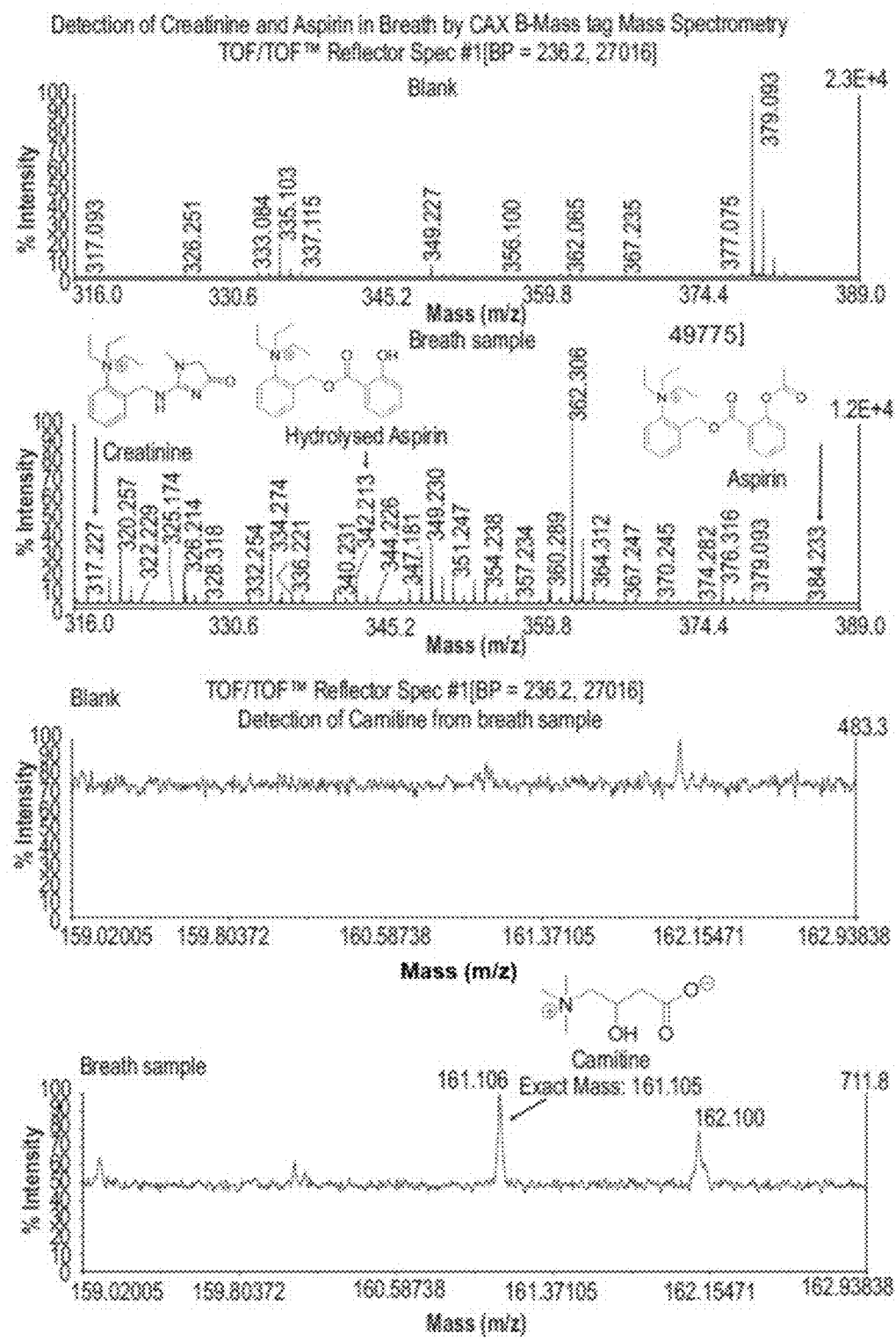
FIG. 3 shows two mass spectra related to detection of aspirin, hydrolyzed aspirin, and creatinine in breath according to General Procedure using CAX-B. The blank is as above.

A SAS can be organic or inorganic. It can be single layered or multilayered or mosaic or combinations of these comprising of ceramic, or carbon, or metal, or metal oxide, or surface treated material, or surface coated material, or silica, or glass, or quartz, or polyethylene, or polypropylene, or polycarbonate, or polyester, or bakelite, or crystals of salts, or surface of a stone or ice, or a dry gel, or zeolite,or polyfluorocarbon, or chitin, or silicon, or mica, or cellulose, or modified cellulose. It can be polar or nonpolar or mixed. It can be ionic or nonionic. It can be porous or nonporous. It can be a semi-solid. It can be an electret. It can be a particle or comprise particles or fibers or wires. It can comprise combinations of these. A SAS can be flexible, such as a filter paper or soft membrane. For example, a SAS can comprise a flat surface as provided by a filter paper or membrane.

Collection of airborne compounds can be done passively or actively, when the air is blown on or through the SAS. Compounds that have accumulated from air onto some other surface [primary surface], such as table or wall, can be swabbed by the SAS to pick up the compounds. The compounds may come from a mist or airborne microorganisms. Compounds from a liquid can be collected on a SAS by adding one or more drops of the liquid to the SAS, or dipping the SAS into the liquid. The liquid can be blood, urine, beer or juice, for example. A SAS can be touched to a piece of food such as cheese, lettuce, fish, or steak, for example, to collect compounds for detection. A SAS can be touched to the skin or tongue of an animal or person, to the window or seat of a car, or to a suitcase to collect compounds for detection. A SAS can be used to help diagnose skin conditions such as melanoma. The skin, preferably after cleaning, can be wetted with a liquid such as isopropanol before a SAS is touched or pressed to it, to enhance collection of metabolites. A SAS can be touched to tissue during surgery to help define the cancerous zone.

A diversity of detection techniques is used to measure sorbed substances on surfaces. Mass spectrometry can provide both qualitative and quantitative information. In this technique, heat, plasma (as in DART), an electrospray (as in DESI) or an organic solvent can be used to recover a sorbed compound from a SAS for detection. When heat, plasma or electrospray is employed, sorbed compounds can be directly volatilized for entry into the mass spectrometer. If the sorbed compounds are eluted from a SAS with an organic solvent, three choices for the subsequent steps are common, and they may be combined to some degree. 1. Direct injection into the mass spectrometer, perhaps via a chromatographic interface; 2. Evaporation of solvents and redissolving of the residue to provide a more concentrated sample of compounds for introduction into the mass spectrometer; and 3. Derivatization of the eluted or eluted/evaporated or eluted/evaporated/ redissolved compounds to improve the volatility or sensitivity of the compounds before they are introduced into the mass spectrometer.

Mass tag mass spectrometry is sometimes used for detection. In this technique, a target compound or type of compound is reacted covalently with a reactive reagent called a "mass tag" to form a covalent mass tag-compound product that is then detected. The main or usual purpose of the mass tag is to increase the response of the target substance in the mass spectrometer. The term "mass tag" refers to a reagent used in derivatization prior to detection by mass spectrometry. Particularly useful is a cationic xylyl (CAX) mass tag since it is an anchimeric-assisted neutral loss mass tag, as has been described (Wang, P., Zhang, Q., Yao, Y., Giese, R. W. [2015] Cationic Xylene Tag for Increasing Sensitivity in Mass Spectrometry, J. Am. Soc. Mass Spectrom. 26, 1713-1721, DOI: 10.1007/s13361-015-1200-4). Also useful are polyfluoroorganic reagents, such as pentafluorobenzyl bromide, and its p-alkoxy or para-H analogues, for detection by electron capture mass spectrometry (Giese, R. W. [1997] Detection of DNA Adducts by Electron Capture Mass Spectrometry, Chem. Res. in Toxicology, 10, 255-270; Giese, R. W. [2000] Electron-capture mass spectrometry: recent advances, J. Chromatogr., 892, 329-346.).

Figure 8:
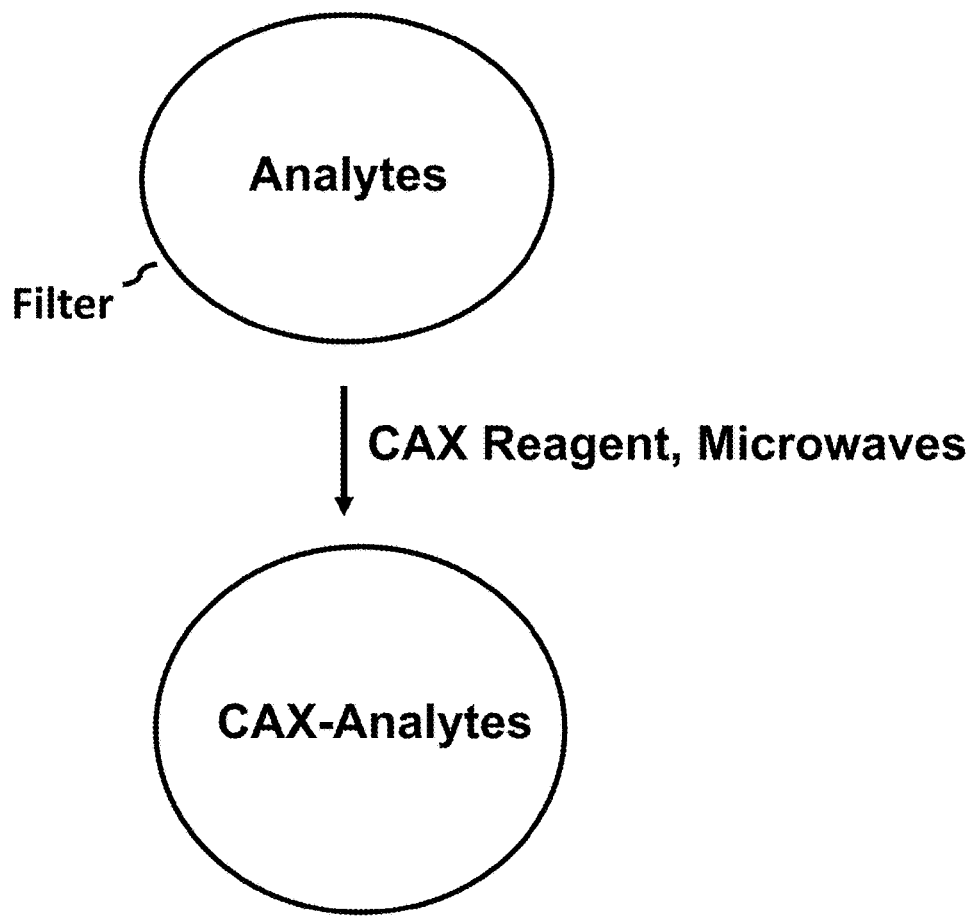
FIG. 8 shows a schematic depiction of a surface tagging reaction on an SAS with a CAX reagent.

Disclosed is a novel process for the detection of sorbed compounds on a SAS by mass spectrometry involving the use of mass tags. In some embodiments, mass tags are quaternary amines and polyfluoroorganic compounds. In one instance of the disclosed method, derivatization is conducted directly on a SAS containing the sorbed compound(s), especially under an energy-rich conditions. This gives a quick and/or convenient derivatization. In certain embodiments, energy types are microwaves and UV. Microwave CAX mass tagging of compounds (Analytes) on a filter SAS is illustrated in FIG. 8. An evaporative derivatization results in solvent on the SAS evaporating during the reaction. An elution solvent then can be employed to recover the mass tag-derivatized compounds for detection. It is useful to elute the mass-tagged compounds with a solvent in which the mass-tagged compounds are more soluble than the residual mass-tag, hydrolyzed mass-tag, or mass-tag that has been reacted with a scavenger. A scavenger is a chemical that converts residual mass-tag to an alternative product. This enables the mass tag derivatives of the sorbed compounds to be detected with minimal interference from residual mass-tag reagent. The present disclosure also covers the case in which a SAS traps residual mass-tag reagent in a covalent or noncovalent way. For example, a mass tag can react both with the sorbed compound on the SAS surface, and the SAS surface itself, to minimize free, residual mass tag after the reaction. A catalyst or catalytic SAS can be used to accelerate the derivatization reaction.

A diversity of energy sources can be used to accelerate the reaction of the mass tag with the sorbed compounds on an SAS, such as: hot surface (e.g. place the SAS on a hot surface, or position the SAS under a hot surface); microwaves (e.g. place the SAS in a microwave oven;), UV (used for nitrene and carbene yielding mass tags), IR, artificial visible light (used especially for a colored SAS that can absorb visible photons), sunlight, heat gun (provides a flow of hot air), ultrasound, electricity (passed through a SAS); inductive heating (SAS is a metal or is nearby or in contact with a metal that is subject to inductive heating; laser (especially when a matrix substance is present as in MALDI mass spectrometry); and an exothermic chemical reaction (conducted as a secondary reaction near the surface, as by employing cordite, thermite or centralite).

Disclosed is use of mass tags having functional groups with restricted reactivity so that sub-classes of sorbed compounds having complementary functional groups can be detected selectively. Examples of such functional groups on mass-tags providing specific detection are anilino, hydrazide, activated carboxyl, hydroxylamine, diazonium, and haloacetyl. The present disclosure additionally covers mass-tags with broad specificity for sorbed compounds to be detected. Examples of broad selectivity reagents, or types of such reagents, are as follows: a quaternary amine benzyl-bromides such as CAX-B (Wang et al., 2015) that can label active hydrogen sites (readily ionizable) on sorbed compounds; pentafluorobenzyl bromide that can similarly label active hydrogen sites, and carbenes or nitrenes that can insert into the chemical bonds of compounds. Carbene and nitrene reactive groups are generated under UV conditions. Broad selectivity can also be achieved by using intense chemical conditions such as cesium hydroxide, phase transfer catalysis, or crown ethers (Dueno, E. E., Che, F., Kim, S-I, Jung, K. W. [1999] Cesium Promoted O-Alkylation of Alcohols for the Efficient Ether Synthesis, Tetrahedron Letters, 40, 1843-1846).

Figure 5:
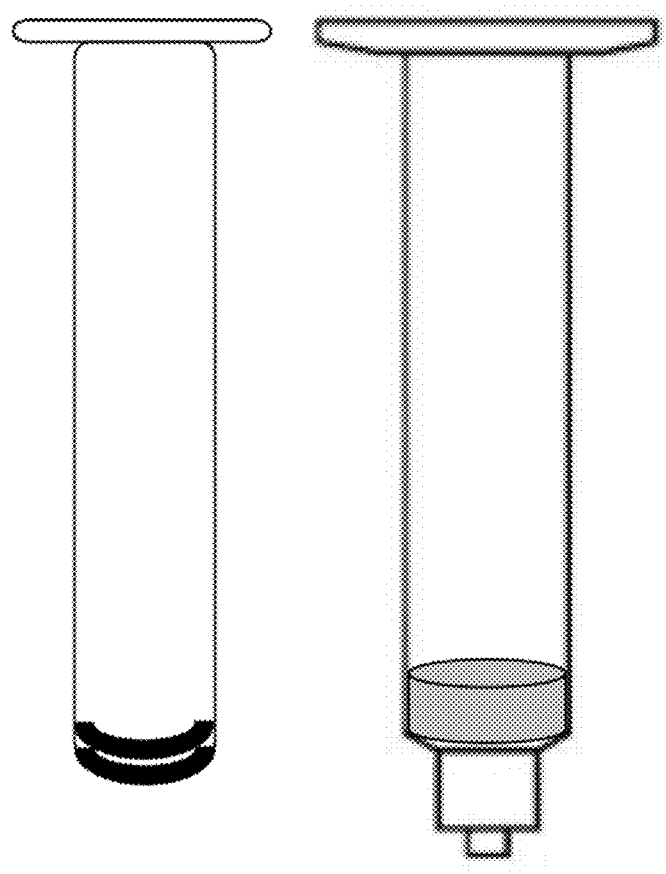
FIG. 5 shows a device comprising filter paper compacted in a syringe for elution of mass-tagged compounds prior to detection.

After the derivatization reaction is conducted on the SAS, it is convenient to elute the products of interest by folding a soft SAS into a tube shape; insert the folded, tube-shaped soft SAS into a syringe; compact the soft SAS using a syringe plunger down to the bottom of the syringe; add an elution solvent to the compressed soft SAS; and recover the elution solvent containing the mass-tagged compounds of interest in one of the following ways: (1) let solvent flow out by gravity; (2) force the solvent out with the aid of the plunger; or (3) force the solvent out by centrifugation. This concept is illustrated in FIG. 5.

Figure 6:
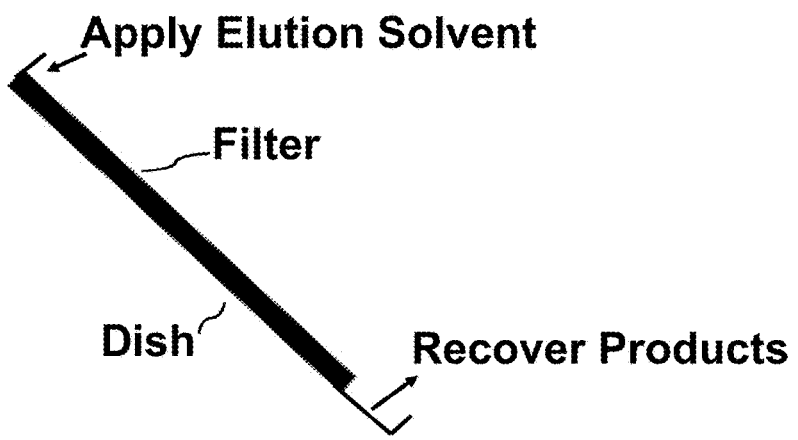
FIG. 6 shows a tilt elution technique where the filter paper is in a watch glass or petri dish.

Another convenient way to elute the mass-tagged compounds from an SAS such as a filter paper is to tilt the container of an SAS, such as a Petri dish or water glass, so that elution solvent added to the upper tip of the SAS flows through the SAS and comes out at the bottom tip of SAS containing the tagged compound(s) of interest. The eluted solution then can undergo analysis by chromatography-mass spectrometry or mass spectrometry. This elution technique can also be made faster by centrifugation. This concept is illustrated in FIG. 6.

Figure 7:
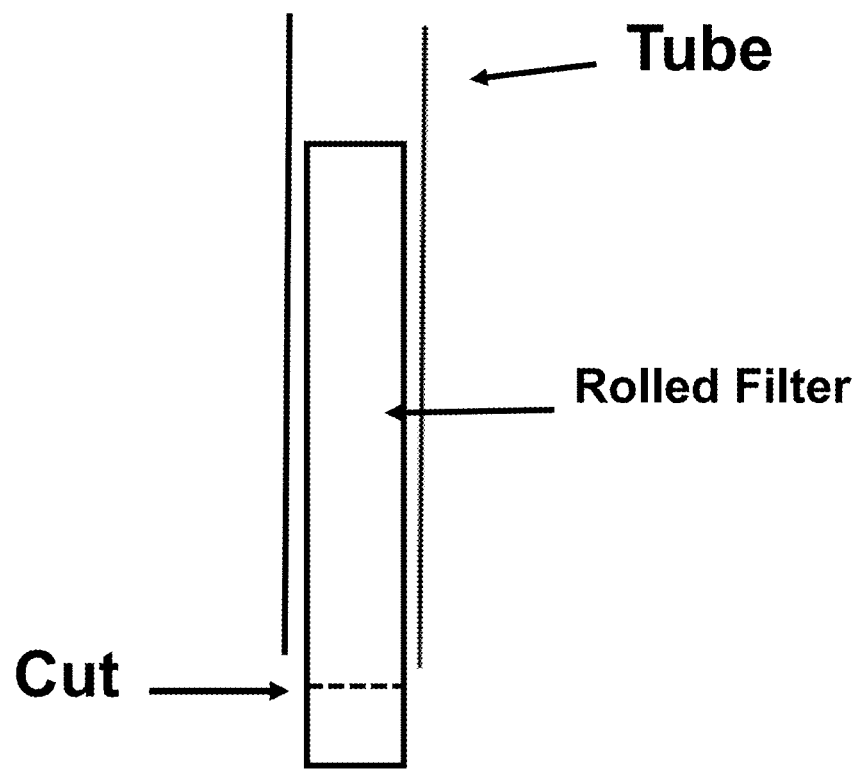
FIG. 7 shows a tube elution device, in the case where the rolled SAS protrudes from the tube.
Figure 14:
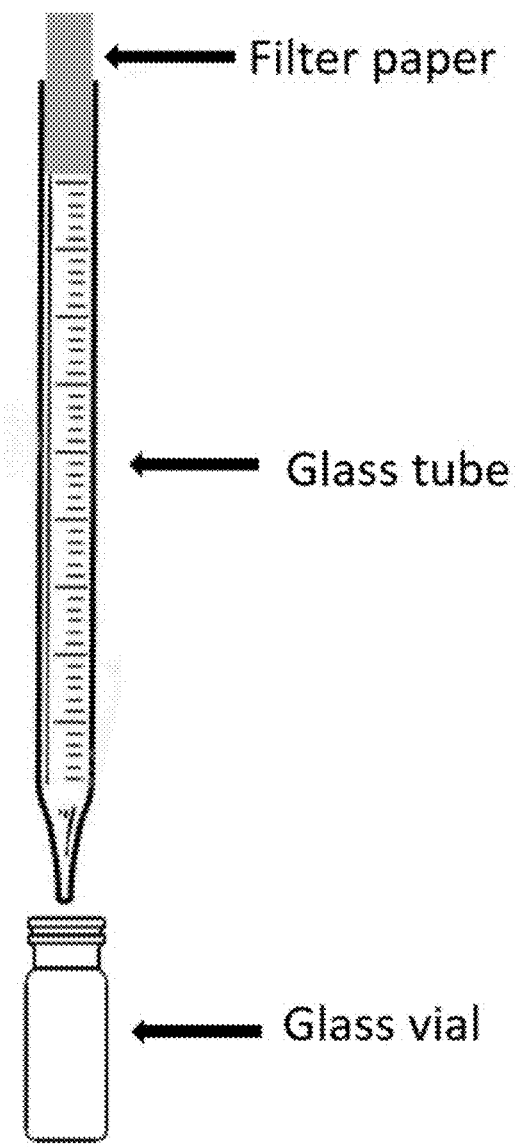
FIG. 14 shows a system for elution of mass-tagged compounds from filter paper, Method 2.
Figure 16:
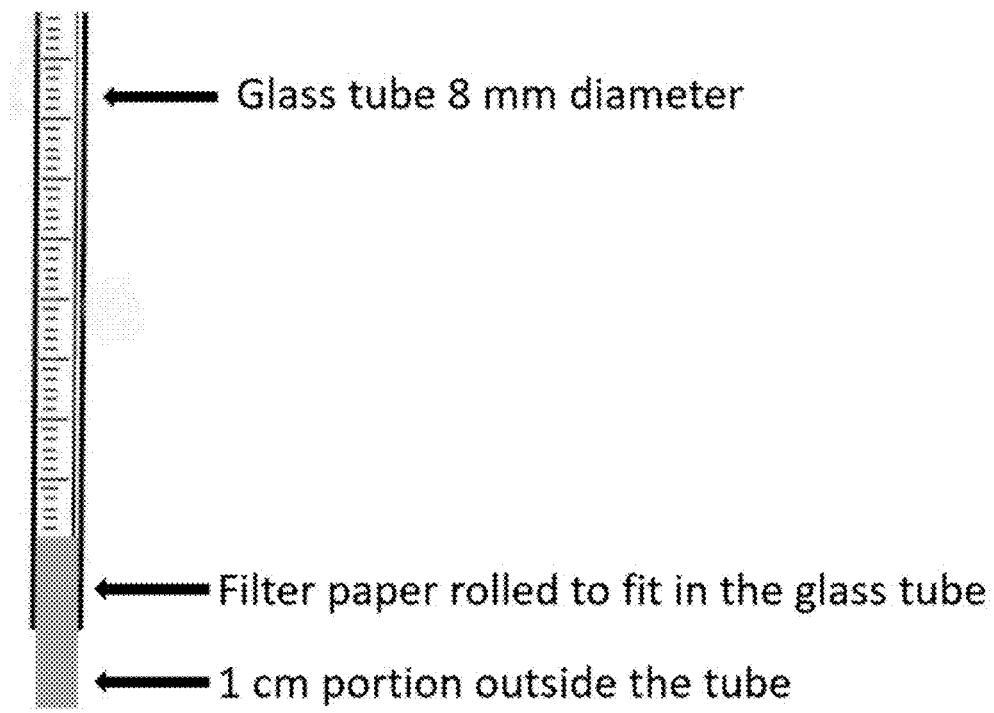
FIG. 16 shows a system for elution of mass-tagged compounds from filter paper, Method 1.

Another convenient way to elute the mass-tagged compounds from an SAS such as a filter paper is to roll the SAS and insert it into a tube with some of the roll sticking out the lower end of the tube. This concept is illustrated in FIGS. 7 and 16. Once the elution solvent has moved the mass-tagged compound(s) of interest onto the part of the surface that protrudes from the tube, this part can be cut off (before or after it has dried), and the products taken from it as by elution. One can also put the rolled SAS into the tube with none of the roll sticking out, and recover mass-tagged compounds by elution. This concept is illustrated in FIG. 14. Potentially this latter elution also can be accelerated by centrifugation.

Because the CAX mass tags have a positive charge and are also nonpolar, one can conduct large-volume liquid injection of eluted CAX mass-tagged compounds from a SAS into a chromatography column under weak solvent elution conditions to achieve enrichment of the CAX masstagged compounds. Such enrichment can take place by hydrophobic retention when the sample is contained in or diluted with water prior to injection. Enrichment can also be done by cation exchange chromatography. For polyfluororganic mass-tagged compounds, enrichment can take place hydrophobically or via fluorous solid phase extraction. For both kinds of mass tags, enrichment can take place on a molecular-imprinted polymer (MIP). A MIP is best directed at a part of the mass tag other than the quaternary amine or polyfluoro part of the residual tag or tag side products to increase purification of desired products. For a polyfluoorganic tag-compound product, detection is best accomplished by gas chromatography electron capture mass spectrometry.

In some embodiments, conditions for derivatization of sorbed compounds (sorbed analytes) on a SAS with a quaternary amine as a mass tag comprise adding such a mass tag directly to the SAS, and then subjecting the SAS to microwaves in a microwave oven, such as 2 minutes on full power. This tends to provide evaporative derivatization conditions, which removes the solvent while accelerating the reaction. Indeed, this established a new technique for derivatization: evaporative phase transfer on-surface derivatization with a quaternary amine reagent. Five key advantages of this new technique are as follows: (1) speed; (2) convenience; (3) solvent removal or reduction in amount; (4) broad scope for analytes (even alcohols are derivatized); and (5) can greatly increase response for analytes in a mass spectrometer. The reaction of the mass tag can take place with the compound-containing SAS in a dish, plate, open tube, test tube or other container. The SAS can be suspended by a pin or clip for this reaction. Elution of the mass-tagged compounds with an organic solvent followed by direct, large volume injection into a chromatography-mass spectrometry system can provide an overall rapid analysis. The masstagged, sorbed compounds on the SAS also can be detected by applying a MALDI matrix such as $\alpha$-cyano-4-hydroxycinnamic acid to the surface and then subjecting this surface to matrix-assisted laser desorption ionization mass spectrometry.

Suitable for detection of a CAX-labeled compound in this disclosure is an electrospray ionization mass spectrometer, especially with a liquid chromatograph at the front end. The mass spectrometer can also be a matrix-assisted laser desorption ionization (MALDI) mass spectrometer. A solution containing a mass-tagged compound eluted off a SAS can be analyzed directly by this latter technique, without any intermittent chromatography.

Figure 9:
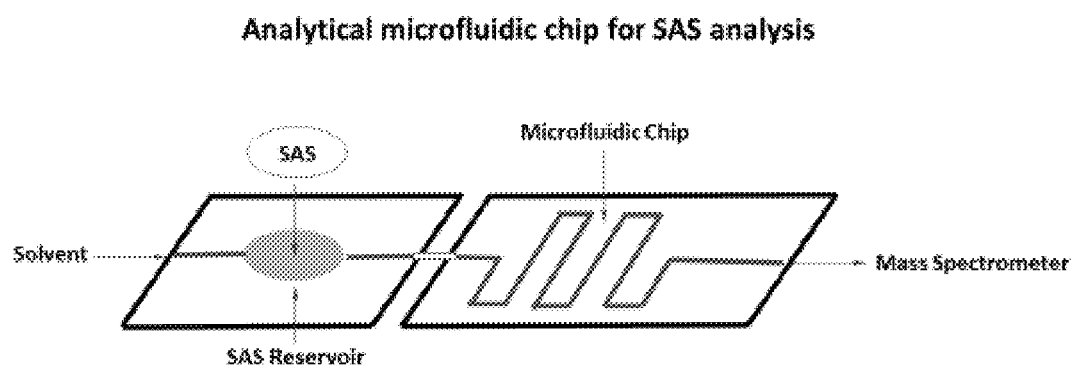
FIG. 9 shows a schematic depiction of an analytical microfluidic chip for analysis via an SAS.
Figure 10:
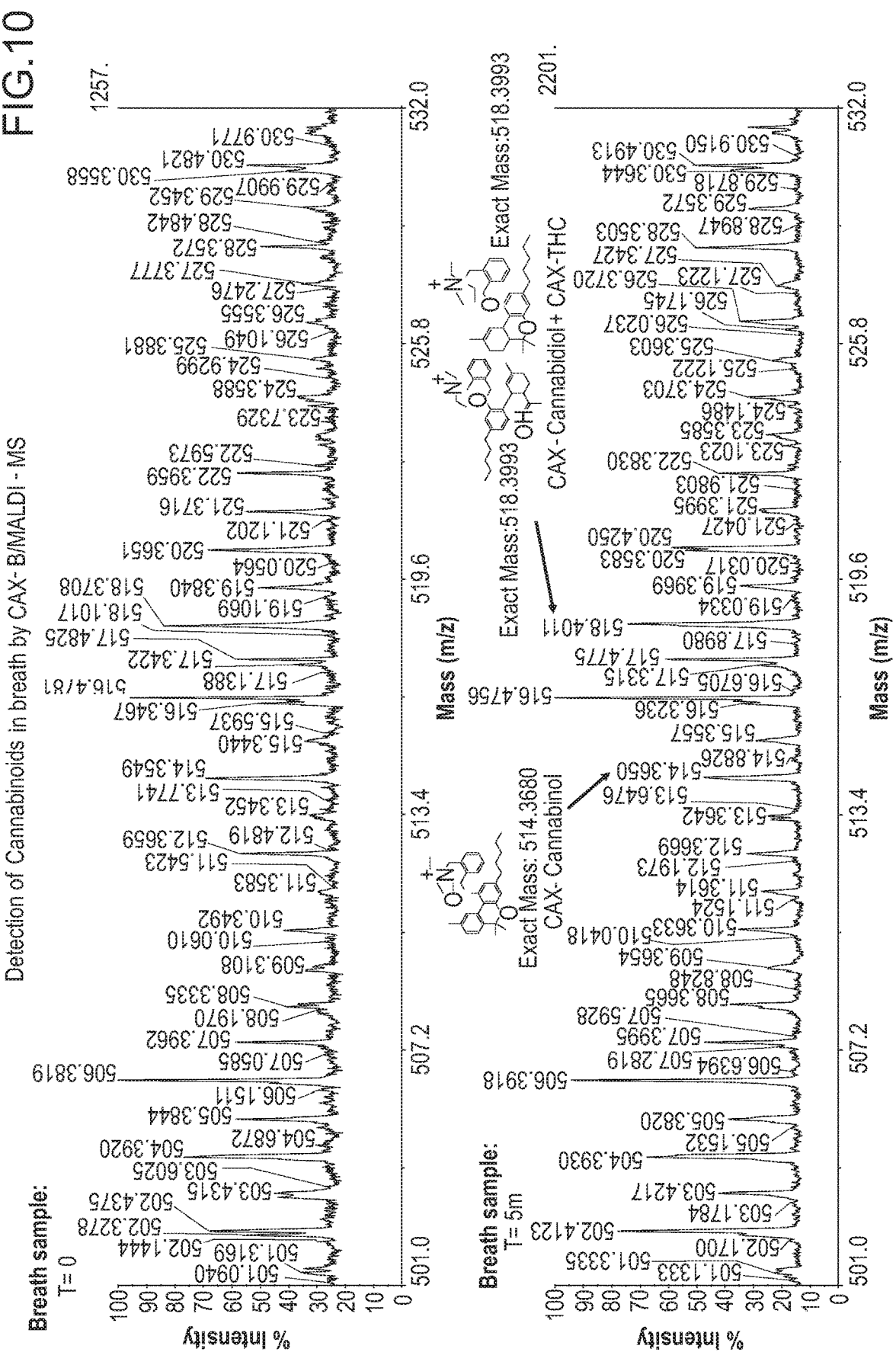
FIG. 10 shows two mass spectra related to preliminary detection of cannabinoids in breath by CAX-B/MALDI-TOF-MS, where the subject who smoked a marijuana cigarette breathed on a filter paper for 5 minutes and the filter paper was tested according to General Procedure Using CAX-B.
Figure 11:
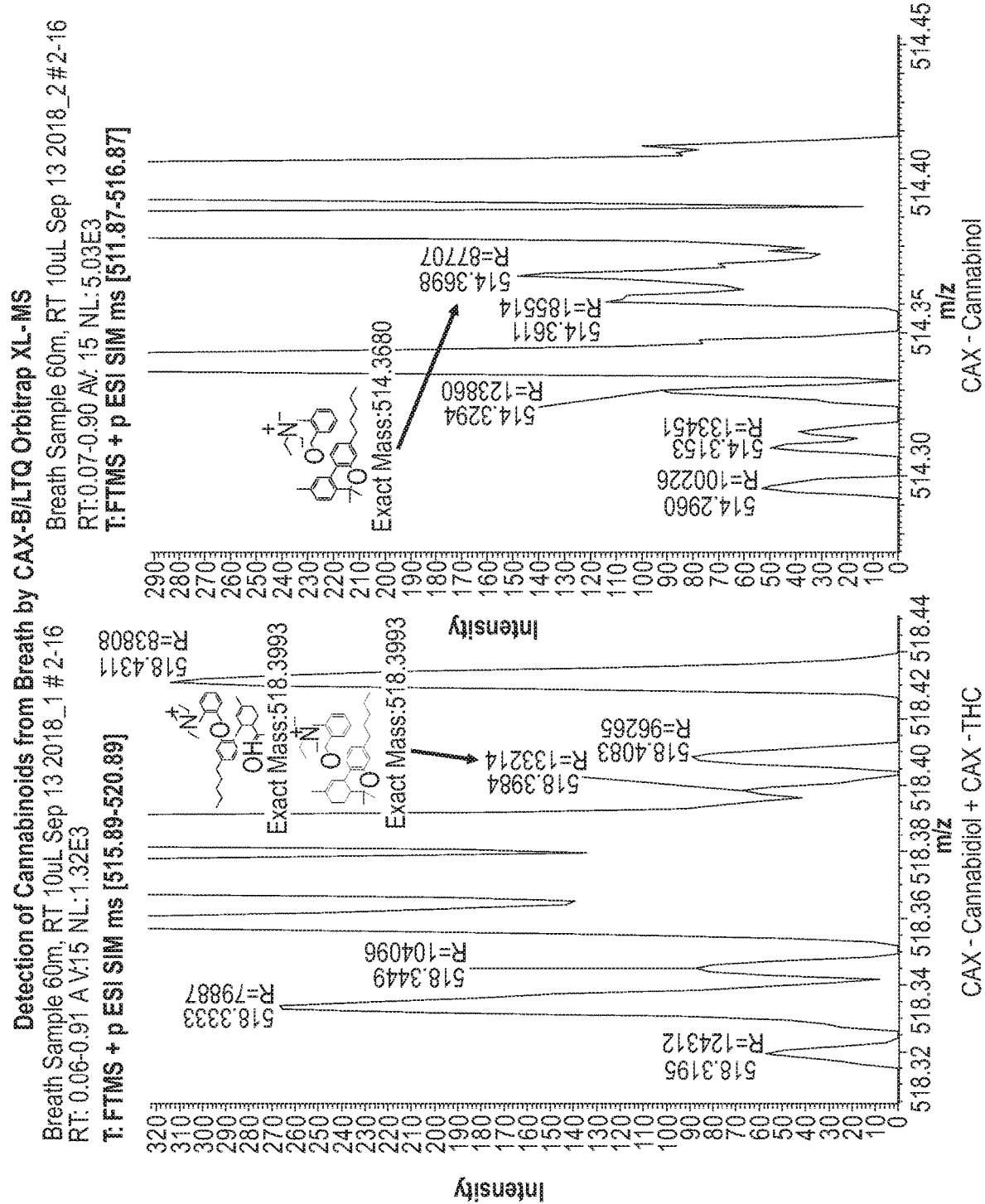
FIG. 11 shows two mass spectra related to preliminary detection of cannabinoids in breath by CAX-B/MALDI-TOF-MS, where the subject who smoked a marijuana cigarette breathed on a filter paper for 5 minutes and the filter paper was tested according to General Procedure Using CAX-B, except that detection was by infusion LTQ Orbitrap XL-MS.
Figure 12:
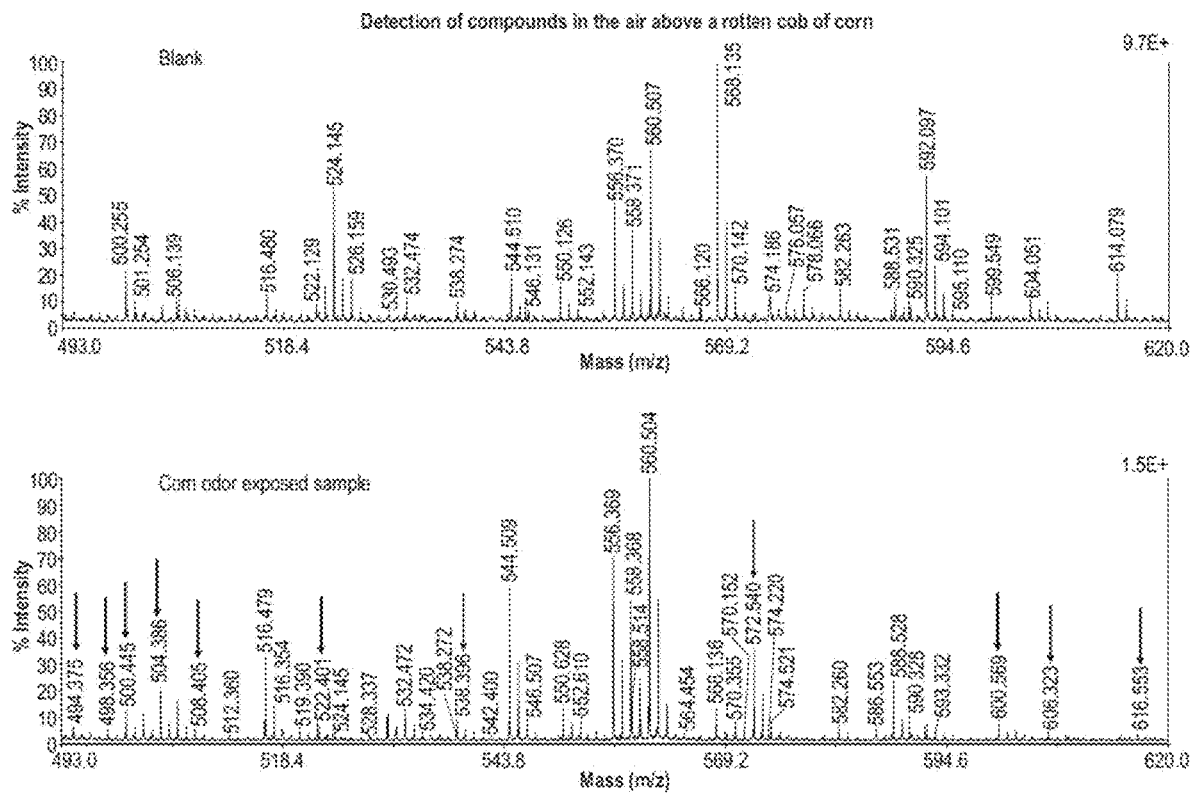
FIG. 12 shows two mass spectra related to detection of compounds in the air above a rotten cob of corn, where a filter paper was kept in a plastic bag along with the corn for 10 minutes, but without and direct contact. The filter paper then was subjected to General Procedure Using CAX-B.
Figure 13:
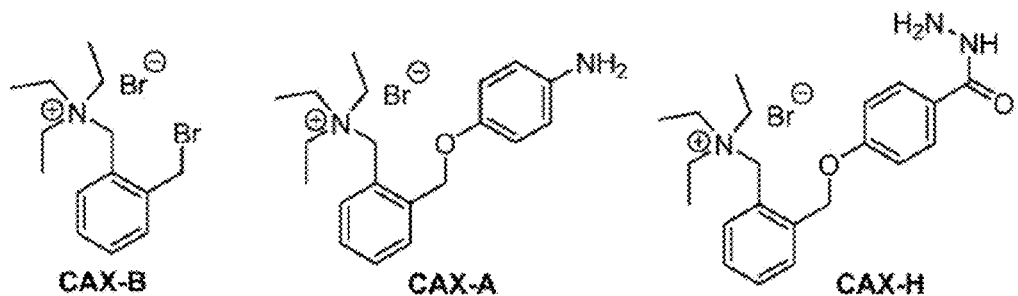
FIG. 13 shows structures of CAX reagents used in General Procedure.

A SAS with collected compounds can be analyzed in a microfluidic chip such as that similar to an Agilent Microfluidic Chip, a Thermo Fisher Scientific Zip Chip, or a New Objective PicoChip. Such a SAS can undergo the mass tagging reaction before or after it is incorporated into or interfaced with a chip. A SAS can be set up as part of a chip prior to collection of compounds (SAS-Chip), where the SAS-Chip is subjected to the following steps: (1) collect compounds to be detected, on the SAS-Chip; (2) undergo mass tagging reaction; and (3) connect to a mass spectrometer or liquid chromatography mass spectrometer for detection. A chromatography column can be part of the chip or the mass spectrometer. FIG. 9 illustrates the concept of loading a SAS into a microfluidic chip followed by elution, preferably by means of enrichment chromatography on-chip into a mass spectrometer.

One aspect of the present disclosure relates to a method for detecting a compound, comprising the steps of: contacting a compound with a solid analytical surface (SAS), thereby forming an SAS with an absorbed compound; contacting the SAS with the absorbed compound with a mass tag, wherein the mass tag reacts with the absorbed compound, thereby forming an SAS with a covalently mass-tagged absorbed compound; and detecting the covalently mass-tagged absorbed compound by mass spectrometry.

In certain embodiments, the SAS comprises a biopolymer, an organic polymer, an inorganic substance, or a metal.

In some embodiments, the compound is a biomolecule, drug, or a synthetic molecule.

In certain embodiments, the compound is a gaseous compound in air or breath.

In certain embodiments, the method further comprises, prior to the detection step, contacting the SAS with the covalently mass-tagged absorbed compound with a solvent, thereby forming a solution comprising the solvent and the covalently mass-tagged absorbed compound; wherein the solvent is selected from the group consisting of methanol, ethanol, isopropanol, acetone, methylisobutylketone, ethyl acetate, acetonitrile, chloroform, dichloromethane, ethylene dichloride, carbon tetrachloride, hexane, cyclohexane, toluene, benzene, xylene, mesitylene, anisole, nitrobenzene, chlorobenzene, dimethylformamide, dioxane, diethyl ether, tetrahydrofuran, 2-methyl tetrahydrofuran, acetic acid, formic acid, propanoic acid, aqueous buffer, salt solution, water, and a combination of any of them.

In some embodiments, the compound is from a food, animal, human, or a cell culture.

In certain embodiments, the mass tag is a molecule comprising a moiety selected from the group consisting of quaternary amine group, a benzyl group, and a polyfluoroorganic group, and the polyfluoroorganic group has at least three fluorine atoms.

In some embodiments, the mass tag is a molecule comprising a moiety selected from the group consisting of

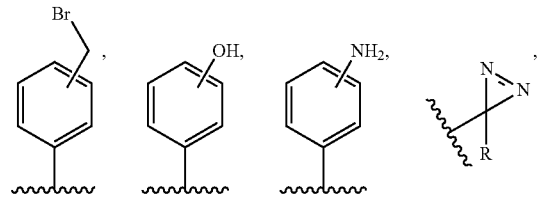

—NHNH$_2$, —C(=O)Hal, —NHOH, —C— (carbene group), —N (nitrene group), —N$_2^+$ (diazonium group), and —C(=O)CH$_2$Hal; Hal is Cl, Br, or I; and R is substituted or unsubstituted C$_{1-6}$ alkyl, C$_{1-6}$ haloalkyl, or C$_{6-12}$ aryl.

In certain embodiments, the SAS comprises an ion exchange surface or a hydrophobic surface.

In some embodiments, the method further comprises folding, compacting or shredding the with the covalently mass-tagged absorbed compound prior to contacting the SAS with the covalently mass-tagged absorbed compound with the solvent.

In certain embodiments, the mass tag reacts with the absorbed compound upon exposure to electromagnetic radiation, such as microwave radiation or UV radiation.

In some embodiments, the reaction takes place under evaporative conditions.

In certain embodiments, the compound is comprised by a liquid sample or a solid sample.

In some embodiments, the mass tag is an anchimeric-assisted neutral loss cationic reagent.

One aspect of the present disclosure relates to a device for collecting breath aerosol, comprising a card or an envelope, wherein the card or the envelope comprise a tab, wherein the tab is a SAS.

In certain embodiments, the tab comprises filter paper, a membrane, or a disc, wherein the disc comprises an inorganic substance.

In some embodiments, the tab is attached to the card or the envelope, thereby forming an attachment, wherein the attachment comprises a staple, fold, pin, glue, slot, or pocket.

In some embodiments, the card comprises cellulose or an organic polymer.

In certain embodiments, the card has dimensions of about 1 inch×4 inch.

In some embodiments, the SAS comprises an electret.

EXAMPLES

Example 1. Use of On-Surface Mass Tagging for Analyte Detection

1A. A threat chemical at disaster site is identified by (1) swabbing the surface of a building with a SAS, (2) conducing derivatization by adding a solution of CAX-B to the SAS and heating in a microwave oven for 2 minutes or less, (3) eluting the resulting CAX-tagged compounds with an organic solvent such as acetonitrile or methanol, and (4) injecting into a liquid chromatography mass spectrometer system or a liquid chromatography tandem mass spectrometer system.

1B. A meat is found to be spoiled, infectious, or poisoned by patting it with an SAS and following steps (2)-(4) of Example 1A.

1C. A subject is found to have early lung cancer by breathing onto an SAS for 2 minutes, and following steps (2)-(4) of Example 1A.

1D. A subject is found to have tuberculosis by following steps of Example 1C.

1E. A subject is found to be under the influence of marijuana when driving erratically by following the steps of Example 1C, leading to the detection of one or more cannabinoids or cannabinoid metabolites.

1F. A person who committed a crime is identified by swabbing him with an SAS; independently swabbing various surfaces (e.g., window, table, chair, door) at the crime scene; following steps (2)-(4) of Example 1A; and detecting a similar pattern of metabolites on both SASs.

1G. A subject is characterized in terms of multi-substance abuse by following the steps of Example 1C and detecting multiple drugs of abuse.

1H. The experiment of Example 1A, 1B, or 1C is done with a CAX reagent in which a quinuclidine moiety is present rather than a triethylamine moiety.

1I. The experiment of Example 1A, 1B, or 1C where the sample-exposed SAS is dried in a microwave oven prior to its reaction with CAX-B.

1J. The experiment of Example 1A, 1B, or 1C where the sample-exposed SAS is loaded into syringe or tube prior to its reaction with CAX-B.

General Procedure Using CAX-A

Breath-exposed filter paper (4.25 cm diameter, Fisher brand catalog No. 09-8-3-6A) was treated with 100 µL of Solution A to cover the entire area. Then place on a watch glass (Corning, Inc. 998575) and heated in a household microwave oven (700 w) for 2 min. Upon cooling to room temperature, it was rolled and stuffed into a glass tube (Fisher catalog No. 13-678-20D) as shown in FIG. 14. 1 mL of CHCl$_3$ was added dropwise. The solvent was collected in the vial below as shown in FIG. 14. CHCl$_3$ was evaporated under vacuum and residue was dissolved in 100 µL CH$_3$CN. Five microliters from this vial were taken and added to 20 µL of a α-cyano-4-hydroxycinnamic acid (CHCA) matrix solution (5 mg/mL in 50% aq. CH$_3$CN), and 0.7 µL of the resulting mixture was loaded per spot on a MALDI-TOF plate, and the MALDI-TOF plate was analyzed in a SCIEX 5800 MALDI-TOF/TOF mass spectrometer in the MALDI-TOF-MS mode with 400 shots per spectrum.

Where: Solution A=CAX-A (1 mg)+NaCNBH$_3$ (10 mg) in 1 mL of 50% aq. CH$_3$CN.

General Procedure Using CAX-B

Breath-exposed filter paper (4.25 cm diameter, Fisher brand catalog No. 09-8-3-6A) was treated with 100 µL of Solution B to cover the entire area. Then place on a watch glass (Corning, Inc. 998575) and heated in a household microwave oven (700 w) for 2 min. Upon cooling to room temperature, it was rolled and stuffed into a glass tube (Fisher catalog No. 13-678-20D) as shown in FIG. 14. 1 mL of CHCl$_3$ was added dropwise. The solvent was collected in the vial below as shown in FIG. 14. CHCl$_3$ was evaporated under vacuum and residue was dissolved in 100 µL CH$_3$CN. Five microliters from this vial were taken and added to 20 µL of the CHCA matrix solution (5 mg/mL in 50% aq. CH$_3$CN), and 0.7 µL of the resulting mixture was loaded per spot on a MALDI-TOF plate and tested as described above.
Where: Solution B=CAX-B (1 mg)+triethylamine (10 µL) in 1 mL of 50% aq. CH$_3$CN.

General Procedure Using CAX-H

Breath-exposed filter paper (4.25 cm diameter, Fisher brand catalog No. 09-8-3-6A) was treated with 100 µL of Solution H to cover the entire area. Then place on a watch glass (Corning, Inc. 998575) and heated in a household microwave oven (700 w) for 2 min. Upon cooling to room temperature, it was rolled and stuffed into a glass tube (Fisher catalog No. 13-678-20D) as shown in FIG. 14. 1 mL of CHCl$_3$ was added dropwise. The solvent was collected in the vial below as shown in FIG. 14. CHCl$_3$ was evaporated under vacuum and residue was dissolved in 100 µL CH$_3$CN. Five microliters from this vial were taken and added to 20 µL of the CHCA matrix solution (5 mg/mL in 50% aq. CH$_3$CN), and 0.7 µL of the resulting
Where: Solution H=CAX-H (1 mg) in 1 mL of 50% aq. CH$_3$CN.

Example 2. Optimizing Recovery of Authentic Product (Methods 1-4)

Figure 15:
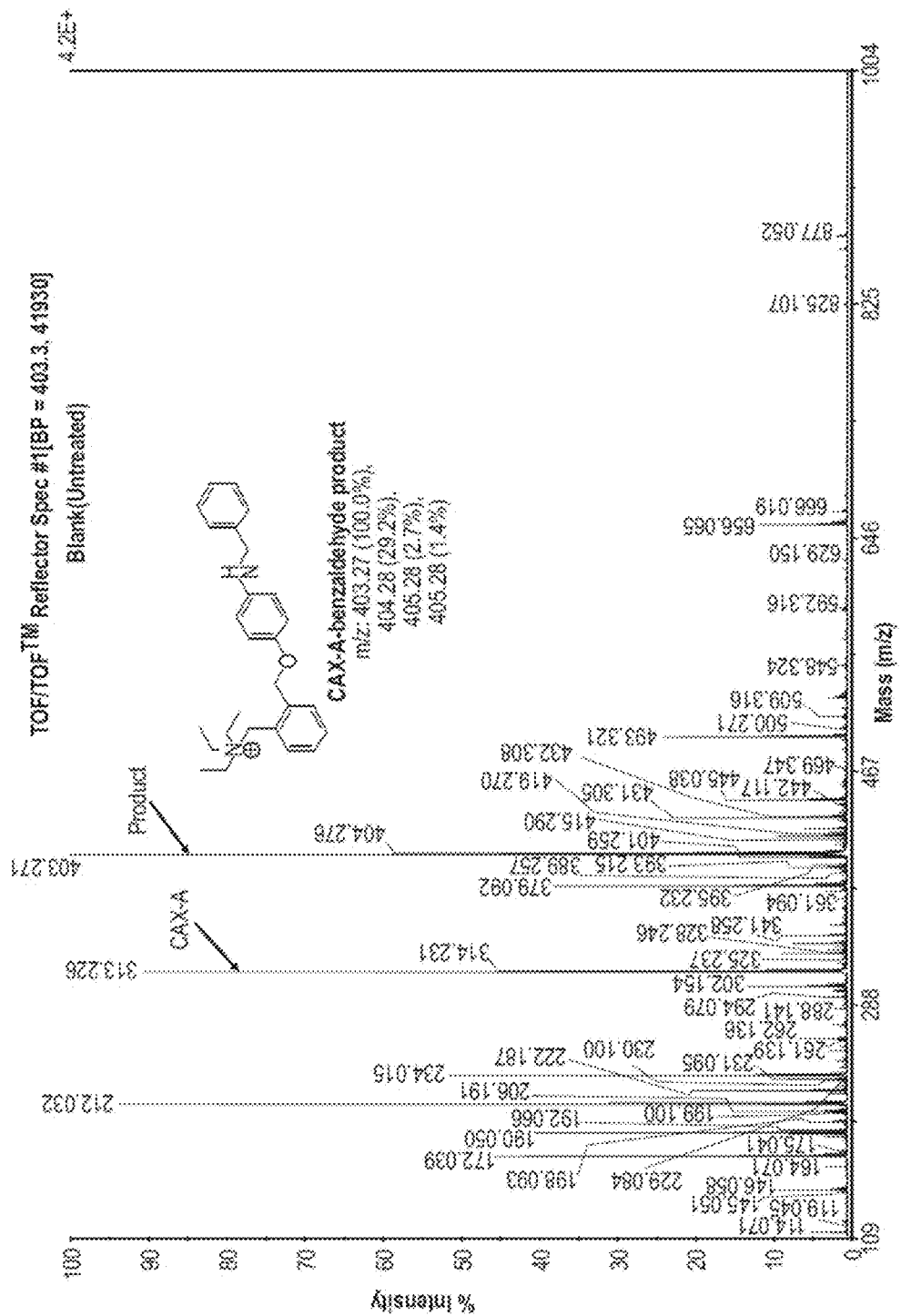
FIG. 15 shows a MALDI-TOF-MS spectrum of an untreated (standard) sample.

General Experimental Details
Solution A2: CAX-A 1.2 mg/mL in 50% aq. CH$_3$CN.
Solution B2: CAX-A-benzaldehyde product (FIG. 15) 1.2 mg/mL in 50% aq. CH$_3$CN.
Solution C2: 5 mg of NaCNBH3 in 250 µL of 50% aq. CH$_3$CN.
Solution D2: 25 µL of solution A2+25 µL of solution B2 were added to solution C2 and stirred for 1 min.

Blank sample (Untreated): 100 µL of solution D2 was placed in a 1 mL vial and evaporated to dryness under vacuum. The residue was dissolved in 400 µL of CH$_3$CN; 5 µL of the CH$_3$CN solution was added to 20 µL of the CHCA matrix solution (5 mg/mL in 50% aq. CH$_3$CN), and 0.7 µL of the resulting mixture was loaded per spot on a MALDI-TOF plate and tested as described above, yielding data shown in FIG. 15.

Method 1

Figure 17:
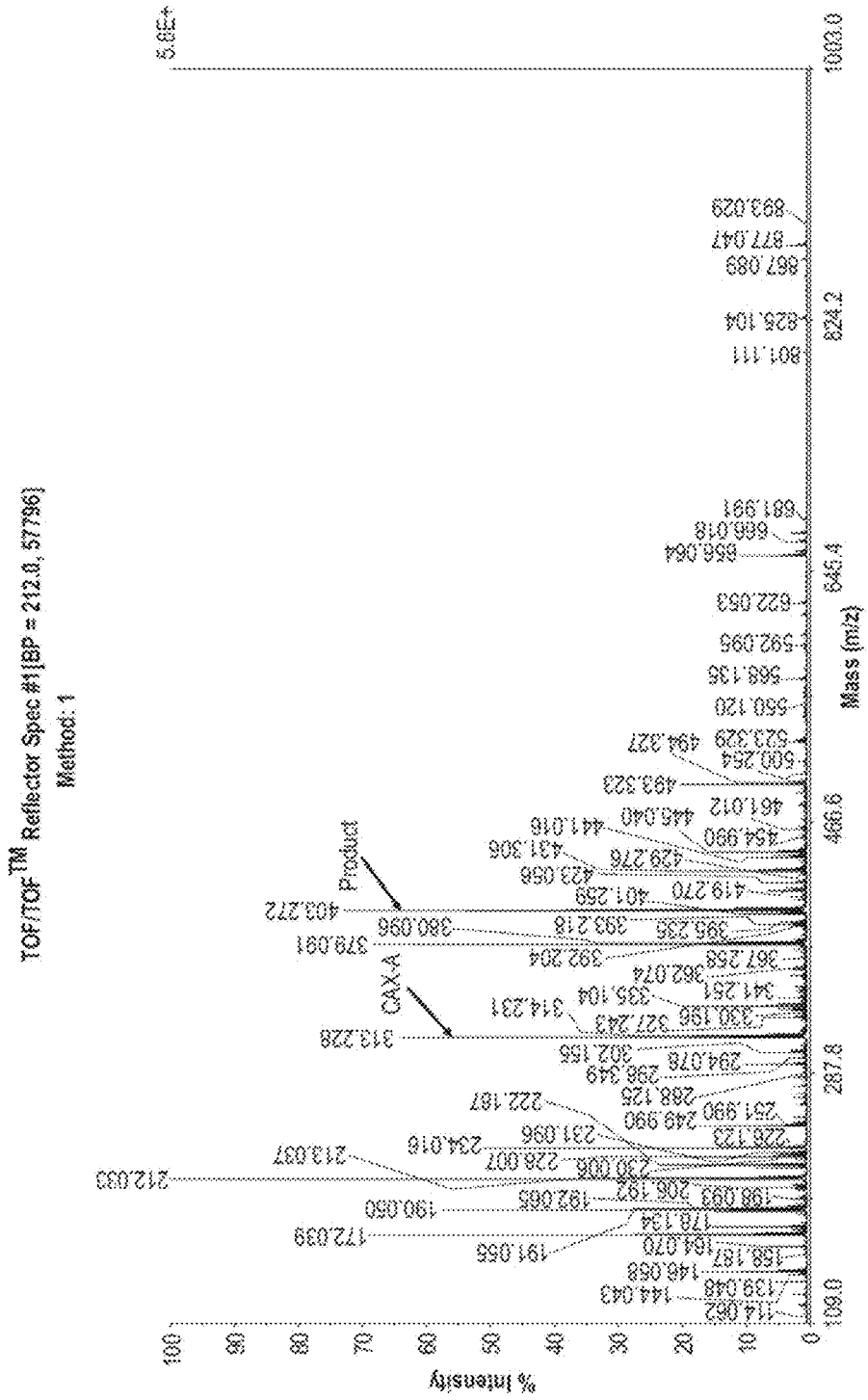
FIG. 17 shows a MALDI-TOF-MS spectrum of a sample obtained by Method 1.

100 µL of solution D2 was added to wet a filter paper (4.25 cm diameter, Fisher brand catalog No. 09-8-3-6A). The paper was placed on a watch glass (Corning, Inc. 998575) and heated under microwave conditions for 2 min. After cooling, it was placed into a cut glass tube (Fisher catalog No. 13-678-20D), as shown in FIG. 16. About 1 cm portion of the paper was protruding out of the tube. To this tube was added 500 µL of CH$_3$CN, when the solvent reached the bottom of the paper, the lower protruding portion was cut, allowed to air dry, and the paper was transferred to a vial containing 400 µL of CH$_3$CN; 5 µL of the CH$_3$CN solution was added to 20 µL of the CHCA matrix solution (5 mg/mL in 50% aq. CH$_3$CN), and 0.7 µL of the resulting sample was loaded per spot on a MALDI-TOF plate and tested as described above. MALDI-TOF-MS spectrum of the sample is shown in FIG. 17.

Method 2

Figure 18:
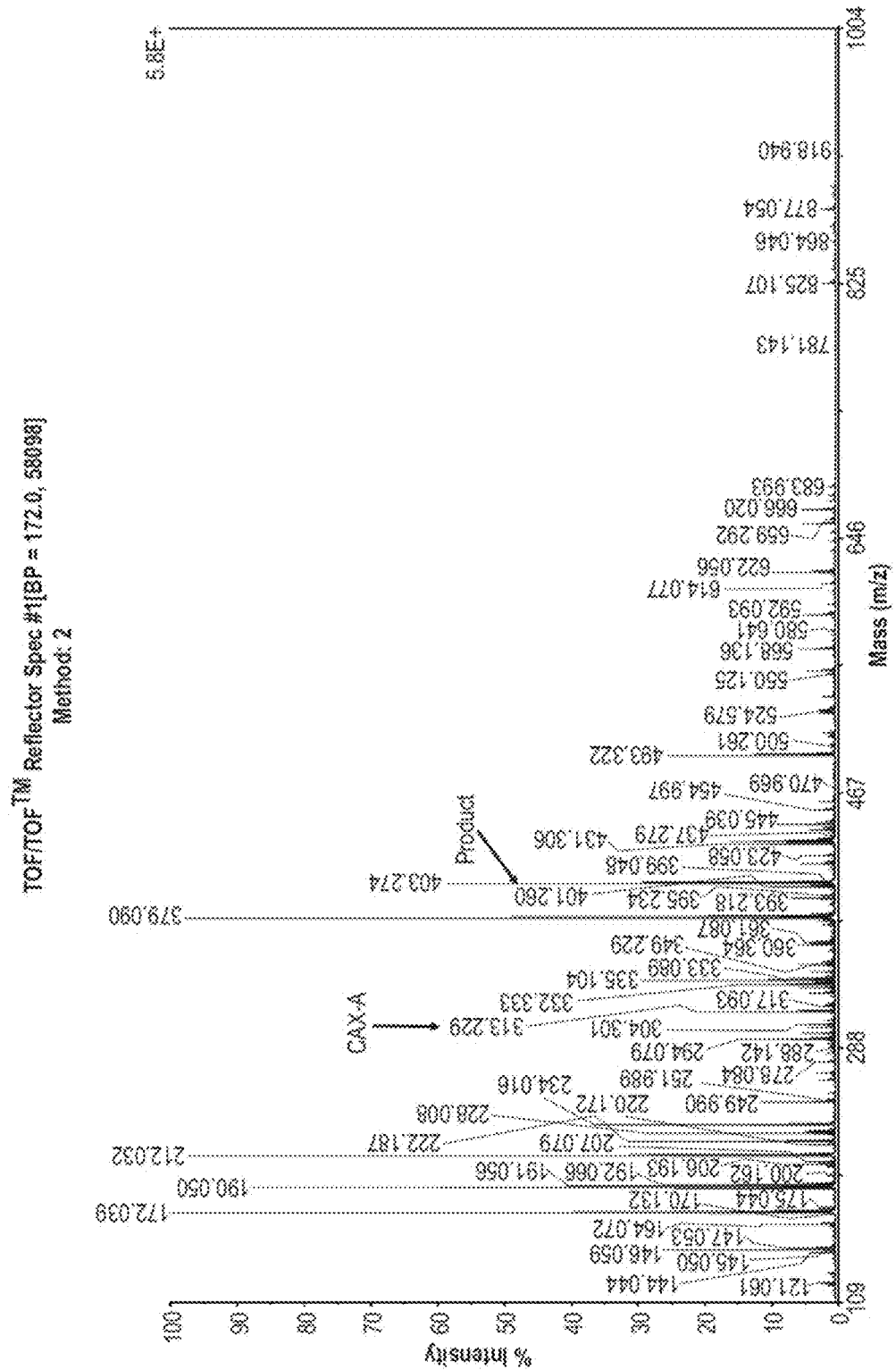
FIG. 18 shows a MALDI-TOF-MS spectrum of a sample obtained by Method 2.

100 µL of solution D2 was added to wet a filter paper (4.25 cm diameter, Fisher brand catalog No. 09-8-3-6A). The paper was placed on a watch glass (Corning, Inc. 998575) and heated under microwave conditions for 2 min. After cooling, it was rolled up and plugged into a glass tube (Fisher catalog No. 13-678-20D), as shown in FIG. 14. To this tube was added 1 mL CHCl$_3$ and the solvent was collected in the vial below. CHCl$_3$ was evaporated under vacuum, and the residue was dissolved 400 µL of CH$_3$CN; 5 µL of the CH$_3$CN solution was added to 20 µL of the CHCA matrix solution (5 mg/mL in 50% aq. CH$_3$CN), and 0.7 µL of the resulting sample was loaded per spot on a MALDI-TOF plate and tested as described above. MALDI-TOF-MS spectrum of the sample is shown in FIG. 18.

Method 3

Figure 19:
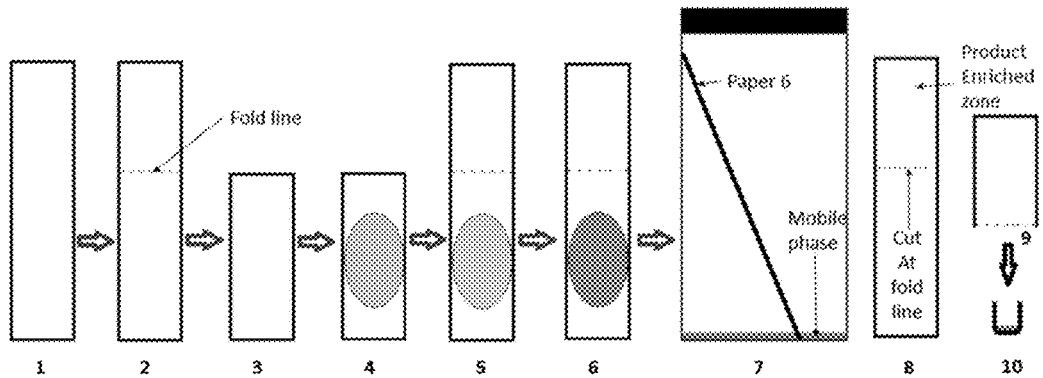
FIG. 19 shows a schematic depiction of Method 3 of sample preparation.
Figure 20:
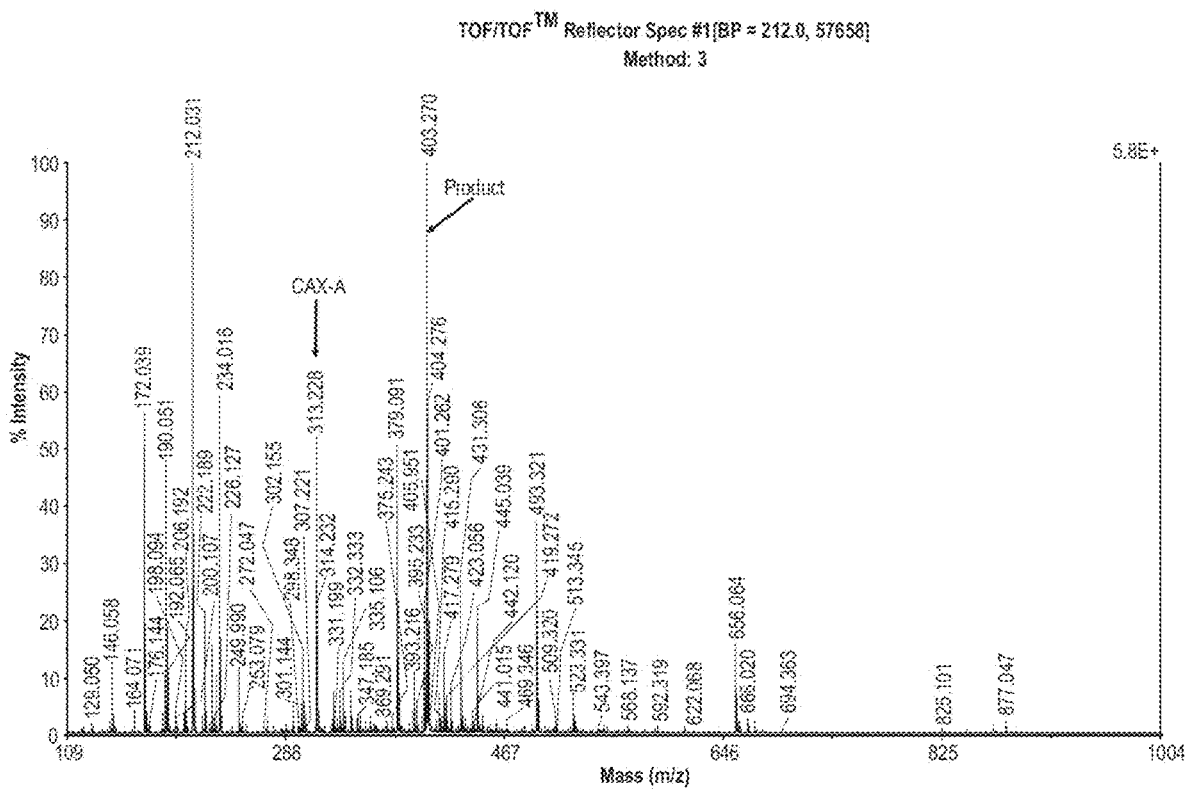
FIG. 20 shows a MALDI-TOF-MS spectrum of a sample obtained by Method 3.

The sample was prepared according to the steps depicted in FIG. 19.
Step 1: A piece of filter paper (1.5"×3.0") was cut;
Step 2: The top portion of the paper was folded along the arbitrary fold line;
Steps 3 and 4: 100 µL of solution D2 was added to an oval zone on the folded filter paper;
Step 5: The paper was placed on a watch glass (Corning, Inc. 998575) and heated under microwave conditions for 2 min;
Step 6: The paper was cooled;
Step 7: The paper was placed into a glass chamber (Pyrex catalog No. 1680-4080; 40×80 mm) and the mixture was eluted using CH$_3$CN as a mobile phase; the solvent was allowed to reach the top of the filter paper;
Step 8: About 2 cm of the top portion of the filter paper was cut (product enriched zone) and allowed to air dry;
Step 9: The paper was transferred to a vial containing 400 µL of CH$_3$CN;
Step 10: 5 µL of the CH$_3$CN solution was added to 20 µL of the CHCA matrix solution (5 mg/mL in 50% aq. CH$_3$CN), and 0.7 µL of the resulting sample was loaded per spot on a MALDI-TOF plate and tested as described above. MALDI-TOF-MS spectrum of the sample is shown in FIG. 20.

Method 4

Figure 21:
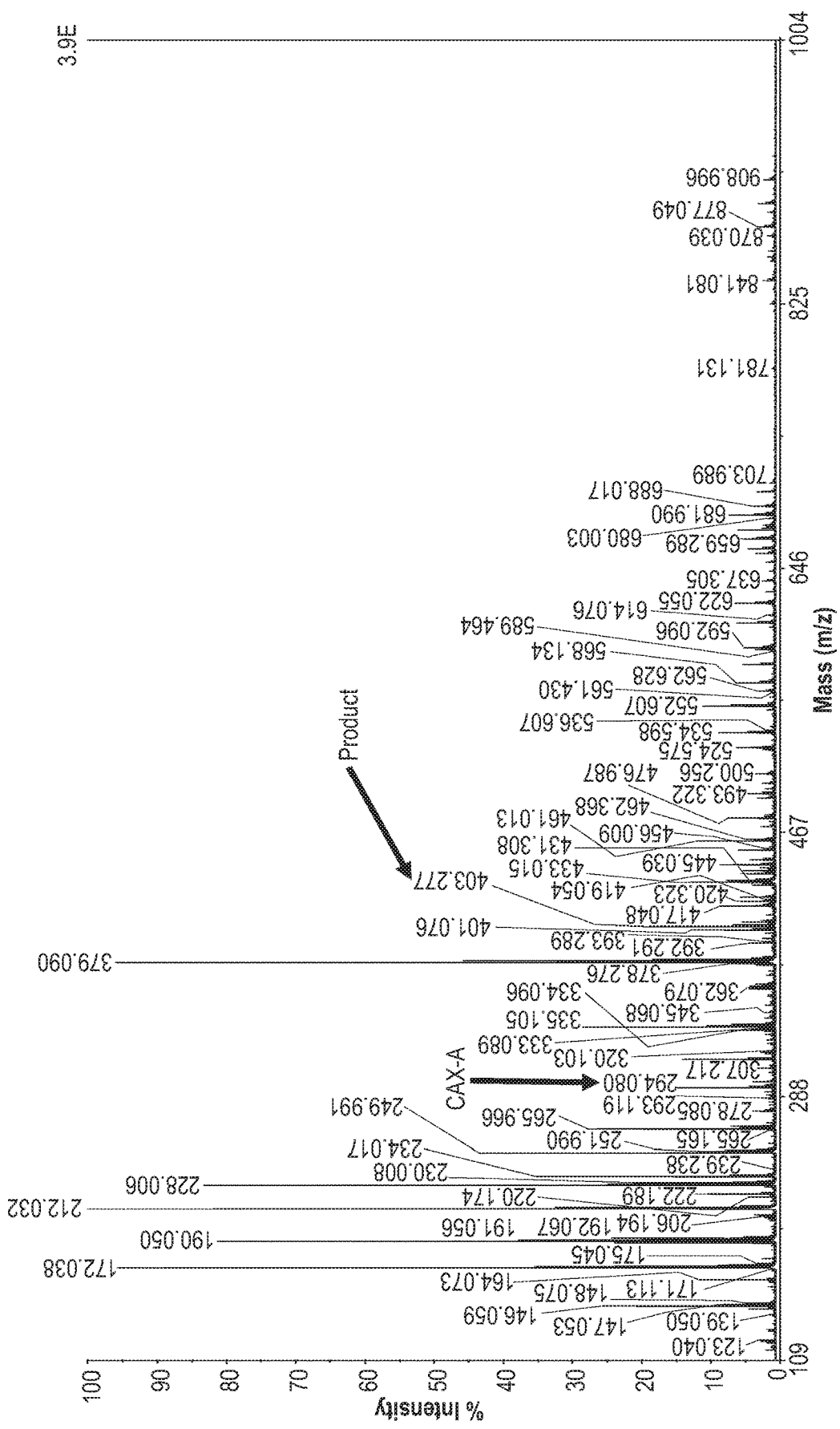
FIG. 21 shows a MALDI-TOF-MS spectrum of a sample obtained by Method 4.

100 µL of solution D2 was added to wet a filter paper (4.25 cm diameter, Fisher brand catalog No. 09-8-3-6A). The filter paper was placed on a watch glass (Corning, Inc. 998575) and heated under microwave conditions for 2 min. After cooling the filter paper was added to a fluted phase separation filter paper and washed with 2 mL of CHCl$_3$. The solvent was collected in the vial below. CHCl$_3$ was evaporated under vacuum, and the residue was dissolved in 400 µL of CH$_3$CN; 5 µL of the CH$_3$CN solution was added to 20 µL of the CHCA matrix solution (5 mg/mL in 50% aq. CH$_3$CN), and 0.7 µL of the resulting sample was loaded per spot on a MALDI-TOF plate and tested as described above. MALDI-TOF-MS spectrum of the sample is shown in FIG. 21.

Example 3. Derivatization and Detection of Acebutolol Using Trifluoromethyl Diazirine Reagent Solution A3: triflluromethyl diazirine reagent (2 µL/mL) and triethylamine (100 µL/mL) in 50% aq. CH$_3$CN) was stored in an amber vial for 4 h before use at rt.

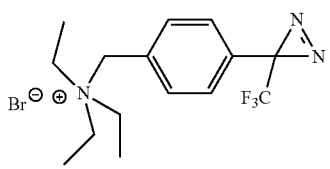

Chemical Formula: C₁₅H₂₁BrF₃N₃
Exact Mass: 379.087
Molecular Weight: 380.253
Trifluoromethyl diazirine reagent Acebutolol solution: 1.7 mg/mL in 50% aq. CH₃CN.

Figure 22:
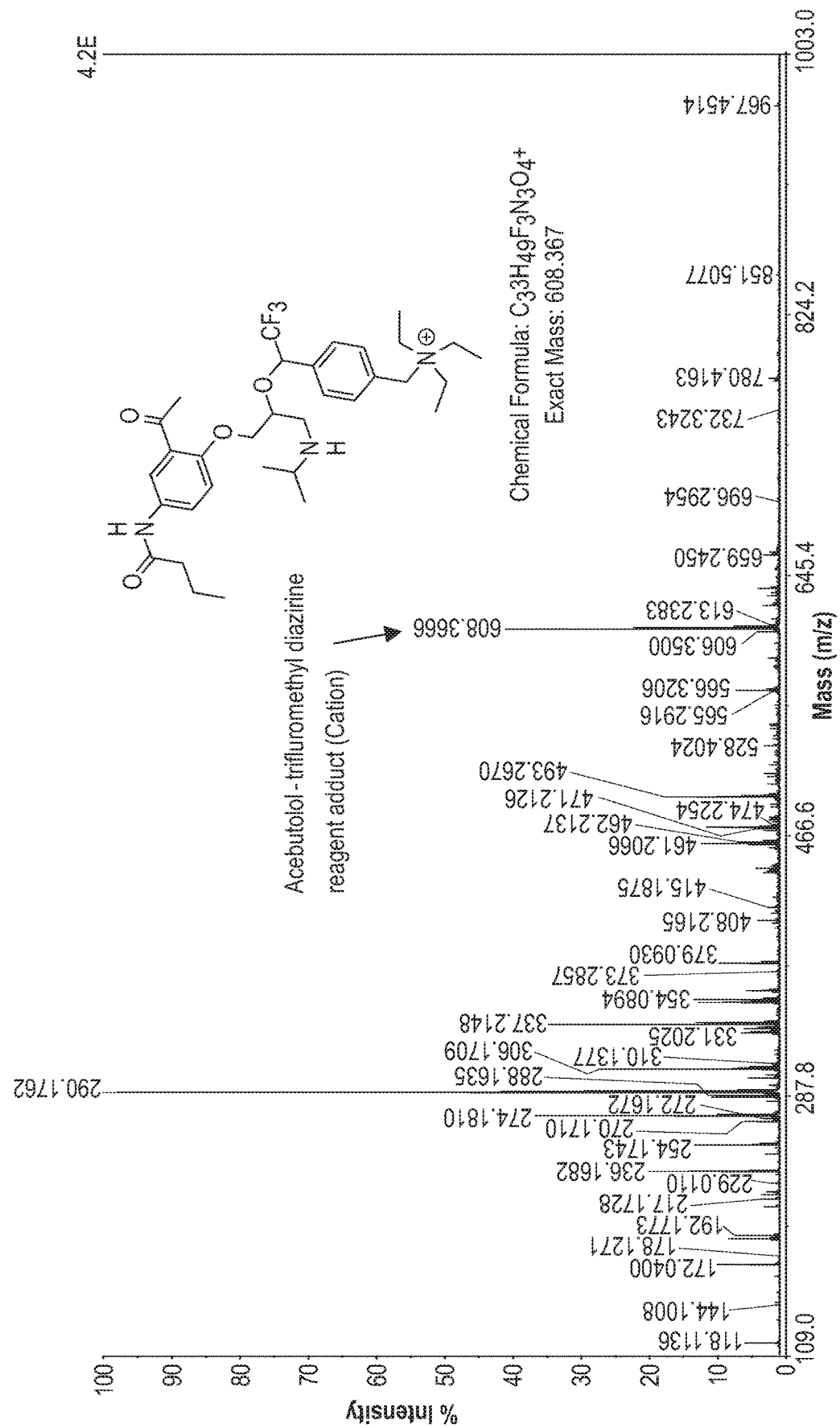
FIG. 22 shows a MALDI-TOF-MS spectrum of a sample obtained in the process of detection of acebutalol using trifluoromethyl diazirine reagent.

A filter paper disc (5 cm in diameter) was wetted with 100 μL of solution A3 and 100 μL of acebutolol solution and kept under UV light (350 nm) for 12 h at r.t. The distance between the UV lamp and the paper was about 2.5 cm. The paper disc was then washed using 2 mL of 50% aq. CH₃CN and 2 mL of isopropanol to give an extract. The extract was separated using a centrifuge. The solvents were removed under vacuum followed by reconstitution of residue by addition of 500 μL of 50% aq. CH₃CN; 2 μL of the CH₃CN solution was added to 500 μL of 5% CHCA matrix solution. 0.55 μL of the resulting sample was loaded per spot on a MALDI-TOF plate and tested as described above. MALDI-TOF-MS spectrum of the sample is shown in FIG. 22. The spectrum demonstrates the presence of a molecular ion for the acebutolol-trifluromethyl diazirine reagent adduct (m/z 608.367), as well as a fragmentation product (m/z 507.404) resulting from the loss of an Et₃N molecule.

Example 4. Detection of Cannabinoids Standard Mix with CAX-B and Ammonium Hydroxide as a Base Reagents:
CAX-B solution: 1.3 mg/mL in 50% aq. CH₃CN;
Ammonium hydroxide: 30% aq. solution
Solution A4: 80 μL of CAX-B solution mixed with 20 μL of ammonium hydroxide solution (used within 1 min)
Cannabinoids standard mix: 1 mg/mL (RESTEK, Catalog No. 34014)

Figure 23:
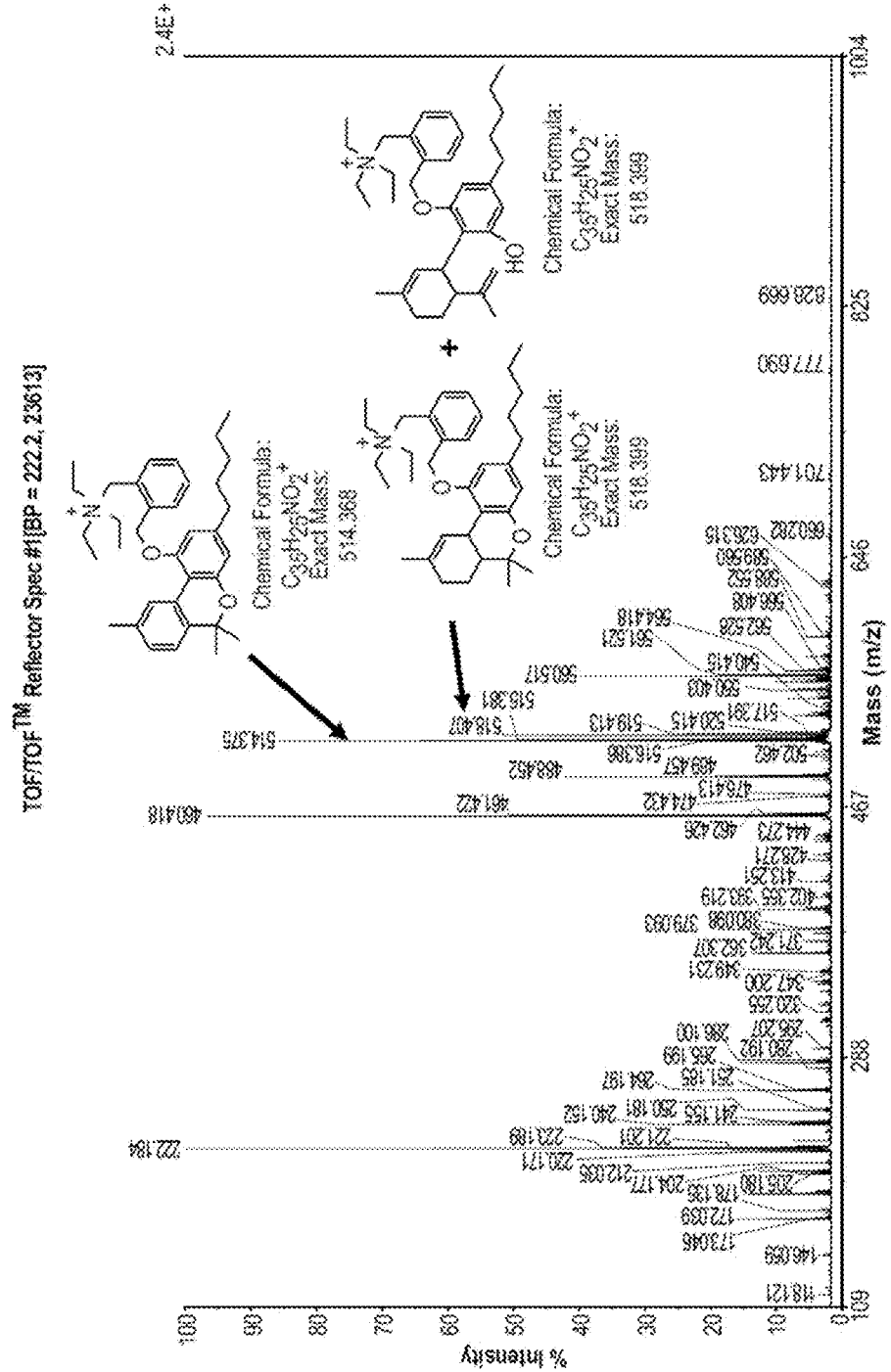
FIG. 23 shows a MALDI-TOF-MS spectrum of a sample obtained in the process of detection of cannabinoids standard mix using CAX-B and ammonium hydroxide as a base.

Procedure:
2 μL of the Cannabinoids standard mix solution was added to a filter paper (Fisherbrand P4 qualitative, Diameter=4.25 cm), and allowed to dry at room temperature. 100 μL of solution A4 was added to the paper, and the paper was placed on a watch glass (Corning, Inc. 998575) and heated under microwave conditions for 2 min. The filter paper was removed using clean forceps and placed in a BD syringe (Mfr. No. 301077, 3mL) and pressed using the syringe plunger to form a plug (FIG. 5). The plunger was withdrawn, 400 μL of CH₃CN were added to the plug, and solvent was collected (under gravity) in a glass vial below. The solvent was evaporated to give a residue which was dissolved in 20 μL of the CHCA matrix solution (5 mg/mL in 50% aq. CH₃CN), and 0.7 μL of the resulting sample was deposited per spot on MALDI-TOF plate and tested as described above. MALDI-TOF-MS spectrum of the sample is shown in FIG. 23. The spectrum demonstrates the presence of a molecular ion for the CAX-B-derivatized cannabinol (m/z 514.368), CAX-B-derivatized cannabidiol (m/z 518.399), and CAX-B-derivatized delta-9-tetrahydrocannabinol (m/z 518.399).

We claim:

1. A method for detecting a compound, comprising the steps of:
contacting a compound with a solid analytical surface (SAS), thereby forming a SAS with an absorbed compound;
contacting the SAS with the absorbed compound with a mass tag, wherein the mass tag reacts with the absorbed compound, thereby forming a SAS with a covalently mass-tagged absorbed compound; and
detecting the covalently mass-tagged absorbed compound by mass spectrometry;
wherein the mass tag is

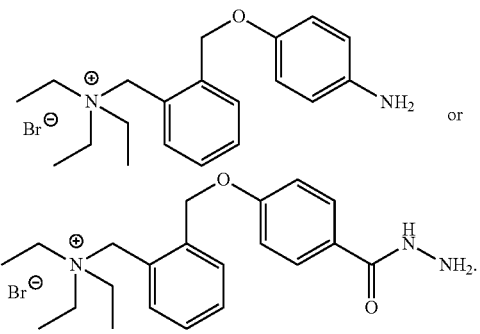

2. The method of claim 1, wherein the SAS comprises a biopolymer, an organic polymer, an inorganic substance, or a metal.

3. The method of claim 1, wherein the compound is a biomolecule, drug, or a synthetic molecule.

4. The method of claim 1, wherein the compound is a gaseous compound in air or breath.

5. The method of claim 1, further comprising, prior to the detection step, contacting the SAS with the covalently mass-tagged absorbed compound with a solvent, thereby forming a solution comprising the solvent and the covalently mass-tagged absorbed compound; wherein the solvent is selected from the group consisting of methanol, ethanol, isopropanol, acetone, methylisobutylketone, ethyl acetate, acetonitrile, chloroform, dichloromethane, ethylene dichloride, carbon tetrachloride, hexane, cyclohexane, toluene, benzene, xylene, mesitylene, anisole, nitrobenzene, chlorobenzene, dimethylformamide, dioxane, diethyl ether, tetrahydrofuran, 2-methyl tetrahydrofuran, acetic acid, formic acid, propanoic acid, aqueous buffer, salt solution, water, and a combination of any of them.

6. The method of claim 1, wherein the compound is from food, an animal, a human, or a cell culture.

7. The method of claim 1, wherein the SAS comprises an ion exchange surface or a hydrophobic surface.

8. The method of claim 5, further comprising folding, compacting or shredding the SAS with the covalently mass-tagged absorbed compound prior to contacting the SAS with the covalently mass-tagged absorbed compound with the solvent.

9. The method of claim 1, wherein the mass tag reacts with the absorbed compound upon exposure to electromagnetic radiation.

10. The method of claim 9, wherein the mass tag reacts with the absorbed compound upon exposure to microwave radiation.

11. The method of claim 9, wherein the mass tag reacts with the absorbed compound upon exposure to ultraviolet radiation.

12. The method of claim 1, wherein the compound is comprised by a liquid sample or a solid sample.

\* \* \* \* \*